(12) United States Patent
Beardsley et al.

(10) Patent No.: US 8,815,585 B2
(45) Date of Patent: Aug. 26, 2014

(54) AUTOMATED METHOD AND APPARATUS FOR EMBRYONIC STEM CELL CULTURE

(75) Inventors: Nathaniel Beardsley, Oregon, WI (US); Veit Bergendahl, Madison, WI (US); Megan Fitzgerald, Madison, WI (US); Christine Daigh, Middleton, WI (US)

(73) Assignee: Cellular Dynamics International, Inc., Madison, WI (US)

( * ) Notice: Subject to any disclaimer, the term of this patent is extended or adjusted under 35 U.S.C. 154(b) by 1137 days.

(21) Appl. No.: 12/164,969

(22) Filed: Jun. 30, 2008

(65) Prior Publication Data

US 2009/0029462 A1 Jan. 29, 2009

Related U.S. Application Data

(60) Provisional application No. 60/947,013, filed on Jun. 29, 2007.

(51) Int. Cl.
*C12N 5/00* (2006.01)
*C12N 5/02* (2006.01)
*C12N 5/071* (2010.01)

(52) U.S. Cl.
USPC ........... 435/375; 435/366; 435/378; 435/380; 435/383; 435/395; 435/397; 435/402

(58) Field of Classification Search
None
See application file for complete search history.

(56) References Cited

U.S. PATENT DOCUMENTS

| 4,352,883 | A | 10/1982 | Lim | 435/178 |
|---|---|---|---|---|
| 4,857,451 | A | 8/1989 | Schwartz | 435/7.24 |
| 4,989,977 | A | 2/1991 | North, Jr. | 356/338 |
| 5,160,974 | A | 11/1992 | Siegel et al. | 356/246 |
| 5,478,722 | A | 12/1995 | Caldwell | 435/1.1 |
| 5,843,780 | A | 12/1998 | Thomson | 435/363 |
| 6,200,806 | B1 | 3/2001 | Thomson | 435/366 |
| 7,029,913 | B2 | 4/2006 | Thomson | 435/363 |
| 7,449,334 | B2 | 11/2008 | Thomson et al. | 435/377 |
| 2006/0198827 | A1 | 9/2006 | Levenberg et al. | 424/93.7 |
| 2006/0210596 | A1 | 9/2006 | Wolf et al. | 424/422 |

FOREIGN PATENT DOCUMENTS

| WO | WO 94/17178 | 8/1994 |
|---|---|---|
| WO | WO 03/087292 | 10/2003 |
| WO | WO 2006/027229 | 3/2006 |

OTHER PUBLICATIONS

Baker, M. (2008) Rat embryonic stem cells created. Nature, published online Dec. 24, 2008, doi: 10.1038/news.2008.1336.*
Brevini et al. (2010) No shortcuts to pig embryonic stem cells. Theriogenology 74: 544-550.*
Cao et al. (2009) Isolation and culture of primary bovine embryonic stem cell colonies by a novel method. Journal of Experimental Zoology 311A: 368-376.*
Paris et al. (2010) Equine embryos and embryonic stem cells: Defining reliable markers of pluripotency. Theriogenology 74: 516-524.*
Schneider et al. (2010) Canine embryonic stem cells: State of the art. Theriogenology 74: 492-497.*
Bajpai et al. (Dec. 2007) Efficient propagation of single cells Accutase-dissociated human embryonic stem cells. Molecular Reproduction and Development 75(5): 818-827.*
Dang et al., "Controlled, scalable embryonic stem cell differentiation culture," *Stem Cells*, 22:275-282, 2004.
Davies et al., "Specificity and mechanism of action of some commonly used protein kinase inhibitors," *Biochem J.*, 351:95-105, 2000.
Ikenoya et al., "Inhibition of rho-kinase-induced myristoylated alanine-rich C kinase substrate (MARCKS) phosphorylation in human neuronal cells by H-1152, a novel and specific Rho-kinase inhibitor," *J. Neurochem.*, 81:9, 2002.
International Search Report and Written Opinion, issued in Application No. PCT/US2008, dated Aug. 20, 2008.
Joannides et al., "Automated mechanical passaging: a novel and efficient method for human embryonic stem cell expansion," *Stem Cells*, 24:230-235, 2006.
Ludwig and Thompson, "Defined culture media for human embryonic stem cells," *In*: Human Cell Culture, Chapter 1, 1-16, 2007.
Ludwig et al., "Derivation of human embryonic stem cells in defined conditions," *Nat. Biotechnol.*, 24:185-187, 2006.
Ludwig et al., "Feeder-independent culture of human embryonic stem cells," *Nat. Biotechnol.*, 3:637-646, 2006.
Sasaki et al., "The novel and specific Rho-kinase inhibitor (S)-(+)-2-methyl-1-[(4-methyl-5-isoquinoline)sulfonyl]-homopiperazine as a probing molecule for Rho-kinase-involved pathway," *Pharmacol. Ther.*, 93:225, 2002.
Takahashi and Yamanaka, "Induction of pluripotent stem cells from mouse embryonic and adult fibroblast cultures by defined factors," *Cell*, 126:663-76, 2006.
Takahashi et al., "Induction of pluripotent stem cells from adult human fibroblasts by defined factors," *Cell*, 131:861-72, 2007.
Terstegge et al., "Automated maintenance of embryonic stem cell cultures," *Biotech. Bioengin.*, 96:195-201, 2007.
Wang et al., "Intestinal uptake and lymphatic absorption of beta-carotene in ferrets: a model for human beta-carotene metabolism," *Am. J. Physiol.*, 263:G480-486, 1992.
Wang et al., "Human urokinase receptor expression is inhibited by amiloride and induced by tumor necrosis factor and phorbol ester in colon cancer cells," *FEBS Letters*, 353:138-142, 1994.
Watanabe et al., "A ROCK inhibitor permits survival of dissociated human embryonic stem cells," *Nat. Biotech.*, 25:681-6, 2007.
Yu et al., "Induced pluripotent stem cell lines derived from human somatic cells," *Science*, 318:1917-1920, 2007.
Office Action issued in Japanese Patent Application No. 2010-515226, mailed Jun. 11, 2013.
Office Communication issued in Australian Patent Application No. 2008272949, dated Apr. 24, 2013.
Office Action issued in Japanese Application No. 2010-515226, mailed Dec. 27, 2013, and English language translation thereof.

* cited by examiner

*Primary Examiner* — Anne-Marie Falk
(74) *Attorney, Agent, or Firm* — Parker Highlander PLLC

(57) ABSTRACT

The invention concerns methods for automated culture of embryonic stem cells (ESCs) such as human ESCs. In some aspects, methods of the invention employ optimized culture media and limited proteolytic treatment of cells to separate cell clusters for expansion. Automated systems for passage and expansion of ESCs are also provided.

58 Claims, 6 Drawing Sheets

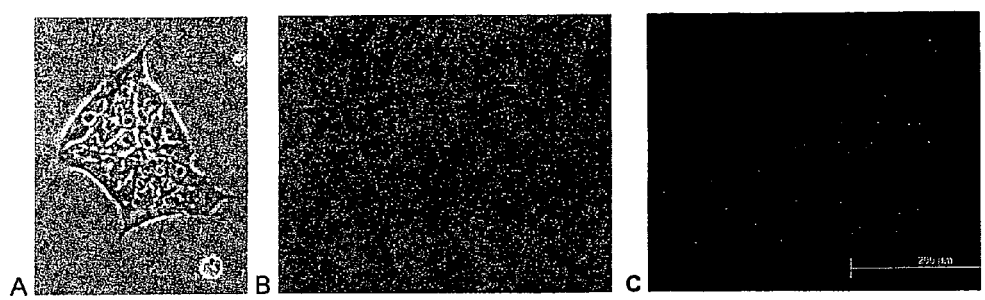
FIGS. 4A-C
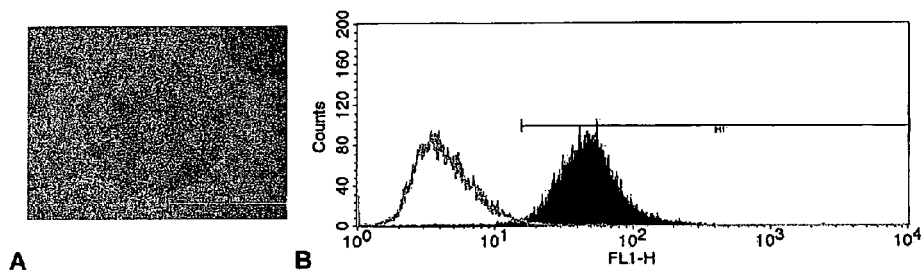
FIGS. 5A-B

AUTOMATED METHOD AND APPARATUS FOR EMBRYONIC STEM CELL CULTURE

This application claims priority to U.S. provisional Application No. 60/947,013 filed on Jun. 29, 2007, the entire disclosure of which is specifically incorporated herein by reference in its entirety without disclaimer.

This invention was made with government support under SBIR#0712181 awarded by the National Science Foundation. The government has certain rights in the invention.

BACKGROUND OF THE INVENTION

1. Field of the Invention

The instant invention concerns mammalian tissue cell culture systems. More specifically, the invention concerns automated stem cells culture systems.

2. Description of Related Art

Since the inception of stable cultures of human embryonic stem cells (ESCs) by Thomson et al. (1998) a growing number of researchers have begun to explore possible therapeutic and diagnostic uses for ESCs. However, even research use of ESCs has strained the limited supplies of ESC cultures. Growing human ES cells is a highly inefficient and variable process since culturing techniques require a high degree of personnel skills and time. Furthermore, the time, labor and complexity of ESC culture has resulted in a very high cost for such cultures. Thus, current methods for stem cell culture are inadequate even for production of sufficient numbers of ECS to satisfy the demands of the research community. Even greater numbers of ESCs will be required to implement a commercially viable therapeutic and diagnostic use of ES cells. Thus, there is need for improved cost effective methods for culture of ESCs.

Previously, methods for automated maintenance of ES cell cultures have been described (Terstegge et al., 2007); however, such methods do not allow ES cell culture to be expanded and thus fail to address the problems associated with large scale ES cell production. Due to immense variability of manual procedures and their limitations towards economical scale-up production of cells, the ability to economically produce high quality cell lineages in large quantities by automation will likely be a crucial criteria that may define success in this very young and promising field. Clearly, there exists a need for improved methods and systems for culture and production of ES cells.

SUMMARY OF THE INVENTION

The present invention overcomes limitations in the prior art by providing methods and compositions for the efficient passage and expansion of embryonic stem cells. In particular embodiments, the invention provides an optimized automated system for the efficient culture and expansion of embryonic stem cells. For instance, in a first embodiment there is provided a method for automated expansion or passage of embryonic stem (ES) cells comprising (a) obtaining a first population of ES cells in growth media, (b) separating the ES cells with an automated separation system and (c) suspending the separated cells in fresh growth media to provide an expanded population of ES cells. In preferred aspects such methods may be used for the passage or expansion of human embryonic stem cells (hESCs). As used herein the term "passage" of cells refers to culture of cells wherein the cells remain viable but may or may not be actively dividing. Furthermore the term "expansion" refers to growth of dividing cells wherein the number of cells increases with culture time.

Methods for obtaining embryonic stem cells, such as human ESCs have been previously described for example see U.S. Pat. Nos. 5,843,780, 6,200,806 and 7,029,913, each incorporated herein by reference.

In certain aspects, the invention concerns cell growth media. For example, in some aspects growth media may comprise serum, such as human or bovine serum. In other aspects, growth media may be defined as serum free media, serum protein free media or protein free media. In various embodiments, no or essentially no differentiation occurs in the cultured expanded ES cells; for example, in the below examples at least 97% of the cultured expanded ES cells remained in an undifferentiated state, based on Oct4 expression. The skilled artisan will understand that media according to the invention may comprise a number constituents including but not limited to vitamins, buffers, glutamine, sugars (e.g., pyruvate), reducing agents (e.g., beta mercaptoethanol), antibiotics, antifungal agents, cytokines or growth factors. Furthermore, in preferred aspects media for use according to the invention may comprise components that reduce apoptosis in disassociated ES cells. For example, media may comprise a Rho-associated kinase (ROCK) inhibitor, such as Y-27632, HA-100, H-1152 or a derivative thereof (Watanabe et al., 2007). Furthermore, in certain aspects, a growth media according to the invention may comprise an effective amount of a ROCK inhibitor, such as an amount that is effective to prevent apoptosis in about or more than about 50%, 60%, 70%, 80%, 90% or 95% of cells during cell separation. In certain further aspects of the invention media may be a "defined media" wherein the exact constituents of the media formulation are known; for example, defined media do not contain "undefined" animal products such as serum, which varies in content between batches. In some very specific aspects, media for use in the invention may be TeSR media, such as defined TeSR media (Table 1; Ludwig & Thompson, 2007; Ludwig et al., 2006).

Various methods for culturing stem cells, e.g., human ESCs, may be used with the present invention. Typically, ESCs are grown in adherent culture systems such as on tissue culture plates. In certain aspects, culture plates for use in the invention may comprise a gel matrix such as a collagen or hydrogel matrix (e.g., a MATRIGEL™). In various embodiments, culture plates may be coated with, e.g., collagen IV, fibronectin, laminin, and vitronectin in combination may be used to provide a solid support for embryonic cell culturing and maintenance, as described in Ludwig et al. (2006). Matrix components which may be used with the present invention to coat tissue culture plates includes a collagen such as collagen IV, laminin, vitronectin, Matrigel™, gelatin, polylysine, thrombospondin (e.g., TSP-1, -2, -3, -4 and/or -5), and/or ProNectin-F™. Three dimensional support matrices for use in tissue culture have been previously described for example in U.S. Publication Nos. 20060198827 and 20060210596, each incorporated herein by reference. The skilled artisan will recognize that in certain aspects adherent tissue culture cells may be defined by the cell density or confluency. Thus, in some cases, methods of the invention involve expansion of proliferating cells from a high density to a lower density to facilitate further cell proliferation. For example, methods for expanding cells according to the invention may involve a first population of ES cells that is between about 50% and 99% confluent. For example, in certain aspects the first population of ES cells may be about or less than about 60%, 70%, 80%, 90% or 95% confluent. Furthermore, in certain aspects expansion or passage of adherent ES cells may involve seeding separated cells in fresh growth media. As used herein the term "seeding" cells means dispersing cells in growth media such that the resultant cell culture(s) are of approximately uniform density. Thus, seeding of cells may involve mixing separated cells with fresh growth media and/or spatially dispersing separated cells over the surface of a tissue culture plate.

Furthermore, in certain aspects, methods of the invention may involve seeding cells to a particular density in fresh media. For example, in some cases, methods may be defined by the relative density used for seeding of separated cells in fresh media. For instance, separated cells may be seeded over a larger plate surface area than the surface area that comprised the first population of ES cells. In preferred aspects, the surface area of a new cell culture plate(s) is about or between about 5 to about 35, between about 10 and about 35, between about 15 and about 30, or between about 28 and about 34, or about 30, 31, or 32 times greater than the surface area of the plate comprising the first population of ES cells. The skilled artisan will recognize that in certain aspects expansion of cells according to the invention involves seeding cells on larger culture plates, however in some cases cells may be seeded on multiple plates wherein new plate surface area is defined as the sum of the surface areas of the plates unto which the separated cells are seeded. Thus, in some aspects, methods of the invention may be used to produce a plurality of cell culture populations from a starting cell culture population.

In some aspects the invention concerns a system for the separation of cells, such as an automated separation system. In certain aspects, ES cells may be mechanically or chemically separated. Chemical separation may be achieved by using chelating molecules (e.g., EDTA, EGTA, citrate or similar molecules that can efficiently chelate or complex calcium and/or magnesium ions). In other embodiments, urea may be used to separate or remove cells from a cell culture plate. Removal of these ions distorts proteins required for attachment of the cells to each other and to the vessel surface. EDTA is present in most Trypsin reagents sold for the purpose of detaching and individualizing cells. Chemicals may be used in final concentrations of from about 0.01 mM to about 100 mM in the media to sufficiently break up and individualize the cells. However, in certain cases, cells separation may be facilitated by contacting the cells with an enzyme such as a proteolytic enzyme. For example, a proteolytic enzyme may be trypsin or trypsin-like proteinase, such as purified or recombinant proteinase. Thus, certain aspects enzymes for use according to the invention may be recombinant enzymes that are essentially free from other human or animal proteins or nucleic acids. In some specific aspects a proteinase for use in the invention may be TRYPLE™. Furthermore, in certain aspects, cells may be contacted with a 1× concentration of TRYPLE™ enzyme solution. The skilled artisan will recognize that concentration of an enzyme used in methods of the invention will depend upon the length of time cells are exposed to the enzyme (i.e., the time cells are exposed to the active enzyme) and the temperature during exposure/incubation. Furthermore, proteins in culture media can reduce the efficacy proteolytic enzymes in separation of cell clusters thus, in certain aspects a cell growth media may be removed prior to contacting cells with a proteolytic enzyme. Thus, in certain aspects, methods of the invention may comprise a system for cell separation comprising (i) removing the media from the first ES cell population, (ii) contacting the ES cell population with a proteolytic enzyme, and (iii) incubating the cell population with a proteolytic enzyme to separate cell clusters. For example, in some cases ES cells are incubated with the proteolytic enzyme or chemical for between about 2 and about 10 minutes such as for about or at most about 3, 4, 5, 6, 7, 8 or 9 minutes. The skilled artisan will also recognize that enzymatic activity is typically temperature dependent thus activity may be modulated by changing the incubation temperature. Thus, in certain aspects, ES cells may be incubated with an enzyme such as trypsin at between about 25° C. and about 40° C., such as at about 26° C., 27° C., 28° C., 29° C., 30° C., 31° C., 32° C., 33° C., 34° C., 35° C., 36° C., 37° C., 38° C. or 39° C.

The skilled artisan will recognize that excessive exposure of cells to a proteolytic enzyme such as trypsin can be detrimental to cell viability. Thus, in certain aspects, proteinase incubation may be monitored to determine the length of the incubation that is required to separate cells from a tissue culture plate or to separate cell clusters. For example, incubation may be monitored via microscopy or by flow cytometry (e.g., to assess the size of cell clusters). Methods for performing flow cytometry are well known in the art see for example, U.S. Pat. Nos. 4,284,412, 4,989,977, 4,498,766, 5,478,722, 4,857,451, 4,774,189, 4,767,206, 4,714,682, 5,160,974, and 4,661,913. In some preferred aspects proteinase incubation may be monitored by a computer and the incubation may be halted (e.g., by addition of a proteinase inhibitor) when optimal cell separation is achieved. Thus, in some cases fresh media for cell dilution or seeding may comprise an enzyme inhibitor, such a protease inhibitor. In certain aspects fresh media for use according to the invention may comprise an inhibitor of the proteolytic enzyme used for cell separation. For example, in preferred aspects, fresh media may comprise an amount of an enzyme inhibitor sufficient to inhibit about or at least about 70%, 80%, 90%, 95%, 98%, 99% or substantially all of enzyme activity. For example, in the case where trypsin is used in cell separation system according to the invention, fresh media for may comprise a trypsin inhibitor such as soybean trypsin inhibitor. For instance, in some very specific aspects, fresh growth media may comprise about 0.5 mg/ml of soybean trypsin inhibitor. In other embodiments natural trypsin inhibitors, such as the ones present in serum may be used with the present invention, e.g., to be included in a media during the splitting of cells. In still further aspects, cell growth media may be further replaced with a media that does not comprise an enzyme inhibitor after the enzyme has been essentially inactivated.

Various other protease inhibitors may be used with the present invention. In most cases dilution of the proteolytic enzyme is sufficient to prevent damage to the cells. Non-limiting examples of protease inhibitors that may be used with the present invention include may be obtained from: serum (e.g., α1-antitrypsin, a ~52 kDa serum trypsin inhibitor), lima beans (e.g., six lima bean inhibitors are known which are ~8-10 kDa), bovine pancreas (e.g., Kunitz inhibitor, also known as aprotinin, ~6.5 kDa), avian egg whites (e.g., ovomucoids are glycoprotein protease inhibitors found in avian egg white, ~8-10 kDa), and/or soybeans (several inhibitors are known, typically ~20.7-22.3 kDa).

In certain preferred aspects, methods according to the invention may be automated. For example, a liquid handler robot may be used to automate the methods described herein. A wide array of liquid handler robots are known in the art and may be used according to the invention, for example see U.S. Pat. No. 6,325,114, incorporated herein by reference in its entirety. In some aspects, a robot for use according to the invention may be a Beckman Coulter BIOMEK® 2000 liquid handler (B2K). Furthermore, it is contemplated that an automated system or apparatus for use according to the invention may comprise a bioreactor wherein fluid transfer and/or cell seeding is mediated by pumps or pressure gradients. As shown in the below examples, an automated apparatus and system was produced for feeding and reproducibly splitting human ESCs; the human ESC's cultured using this apparatus and system were of high quality and did not display significant differentiation (greater than 97% undifferentiated, as measured by Oct4 FACS analysis). While the specific cells used in the below examples were human ESC's, the inventors anticipate that other human or mammalian stem cells or iPS cells may be cultured, expanded, and maintained in an undifferentiated state according to the present invention.

In various embodiments, the methods of the present invention may be used to screen compounds which may modulate the differentiation state of a cell. As shown in the below examples, the inventors have demonstrated successfully that this technology may be used for human ESC cell culture-based small molecule screening using defined culture conditions. In certain embodiments, the methods, apparatus and systems of the present invention may be used to screen one or more candidate compound(s) which may affect the differentiation state of a cell. For example, the candidate compound may promote differentiation of a stem cell towards a specific lineage (e.g., hematopoietic, etc.). In other embodiments, the candidate compound may promote de-differentiation or maintain a de-differentiated state in a cell (e.g., promote the generation of an iPS cell from a fibroblast or other cell).

In still further aspects, methods of the invention may comprise an apparatus or system for separating cells comprising a combination or mechanical separation and enzymatic separation. For example, in some cases, cells may be incubated with an enzyme such as trypsin followed by mechanical agitation to further separate cell clusters. For example, mechanical agitation may comprise subjecting cells to shear forces, such as by pipetting the cells repeatedly through an aperture.

The skilled artisan will recognize that a number of ES cell culture system comprises "feeder cells" that supply, in trans, factors that mediate ES cell growth and/or differentiation. However, in certain aspects, methods of the invention concern a population of ES cells that is essentially free from non-ES cells or essentially free from non-human cells.

In still further embodiments, a method of the invention may be defined as an automated method for serial expansion of embryonic stem (ES) cells comprising (a) obtaining a first population of ES cells in growth media, (b) separating the ES cells with an automated separation system, (c) suspending the separated cells in fresh growth media to provide an expanded population of ES cells, (d) incubating the expanded ES cell population under conditions supporting cell growth and (e) repeating steps b-d one or ore times to provide a serially expanded population of ES cells. Thus, methods of the invention may be used for the passage or expansion of a population of stem cells for any number of passages from initial ES culture to senescence of the cells.

In still a further embodiment of the invention there is provided a system for automated expansion of ES cells comprising an incubator, a liquid handler unit and an operating program for cell separation. For example, an operating program may comprise steps for (i) removing media from a first ES cell population, (ii) contacting ES cells with a proteolytic enzyme, (iii) incubating the cells with a proteolytic enzyme to separate cell clusters and/or (iv) subjecting the incubated cells to mechanical agitation to further separate cell clusters. Thus, in some aspects, an operating program may be used to move cells and or fluids between different chambers in the system. In some aspects, cell culture plates may be moved for one chamber to another (e.g., into or out of an incubator). Thus, in certain aspects, a liquid handler may comprise a gripper tool and a liquid handling tool. In still further aspects a liquid handling tool may be an essentially closed system or apparatus wherein cells and/or fluids are moved between chambers by a pressure gradient.

It is anticipated that virtually any pluripotent stem cell or cell line, e.g., human embryonic stem cells or induced pluripotent stem cells (iPS cells), may be cultured via the present invention. For example, human embryonic stem cell line H1, H9, hES2, hES3, hES4, hES5, hES6, BG01, BG02, BG03, HSF1, HSF6, H1, H7, H9, H13B, and/or H14 etc. may be used with the present invention. It is further anticipated that stem cell lines which subsequently become available may also be used with the present invention. Although human embryonic stem cells are preferably used with the present invention, in some instances it may also be possible to use other embryonic stem cells, such as mammal, mouse, primate, etc. with the present invention.

As would be appreciated by one of skill, induced pluripotent stem cells, commonly abbreviated as iPS cells or iPSCs, are a type of pluripotent stem cell artificially derived from a non-pluripotent cell, typically an adult somatic cell, by inserting certain genes. Induced pluripotent stem cells are believed to be identical to natural pluripotent stem cells, such as embryonic stem cells in many respects, such as in terms of the expression of certain stem cell genes and proteins, chromatin methylation patterns, doubling time, embryoid body formation, teratoma formation, viable chimera formation, and potency and differentiability, but the full extent of their relation to natural pluripotent stem cells is still being assessed. IPS cells have been described previously (see, e.g., Takahashi et al., 2006; Takahashi et al., 2007; Yu et al, 2007).

Embodiments discussed in the context of a methods and/or composition of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawing is part of the present specification and is included to further demonstrate certain aspects of the present invention. The invention may be better understood by reference to the drawings in combination with the detailed description of specific embodiments presented herein.

FIG. 3A, depicts an example of an open automated incubator (Cytomat 6000) next to the Platecrane XT (Hudson) connecting the liquid handler (Biomek2000). FIG. 3B depicts an example of the closed Cytomat 6000 on the left side of the system, the Biomek2000 from the back in the middle, and below a temperature control unit. The Stacker of the Biomek2000 system is placed on the right side of the system. FIG. 3C depicts a single channel wash tool used initially to aspirate spent media and feed 4-well or 8 well plates. In the back behind the 4-well plate a 6-well plate is used to serve as a reservoir for trypsin. FIG. 3D depicts an 8-channel tool (P200) used in certain examples to mix and dispense the trypsinized and individualized HES cells from a 4-well mother plate to an 8-well daughter plate in the final split.

FIGS. 4A-C: Phase contrast microscopy pictures of human ES cells after feeding. FIG. 4A, 20× magnification of a single 2-days old human ES cell colony. FIG. 4B, 4× magnification of a 2-days old culture to show the distribution and density of the cultured cells. FIG. 4C, A H1 culture after 5 days of feeding at 4× magnification.

FIGS. 5A-B: Phase contrast microscopy picture of human ES cells after 1000-fold expansion. FIG. 5A, 4× magnification of human ES cell colonies 6-days after the 2nd passage in the scale-up. FIG. 5B, Oct4 analysis by FACS. The left band shows cells treated with the labeled IgG control to show the background and the solid band represents the Oct4 positive population from plate 2 pooled and stained. Both analyses showed greater than 97% Oct4 positive population, suggesting that the automated procedure effectively maintains pluripotent cells in an undifferentiated state.

DETAILED DESCRIPTION OF THE INVENTION

Figure 1:
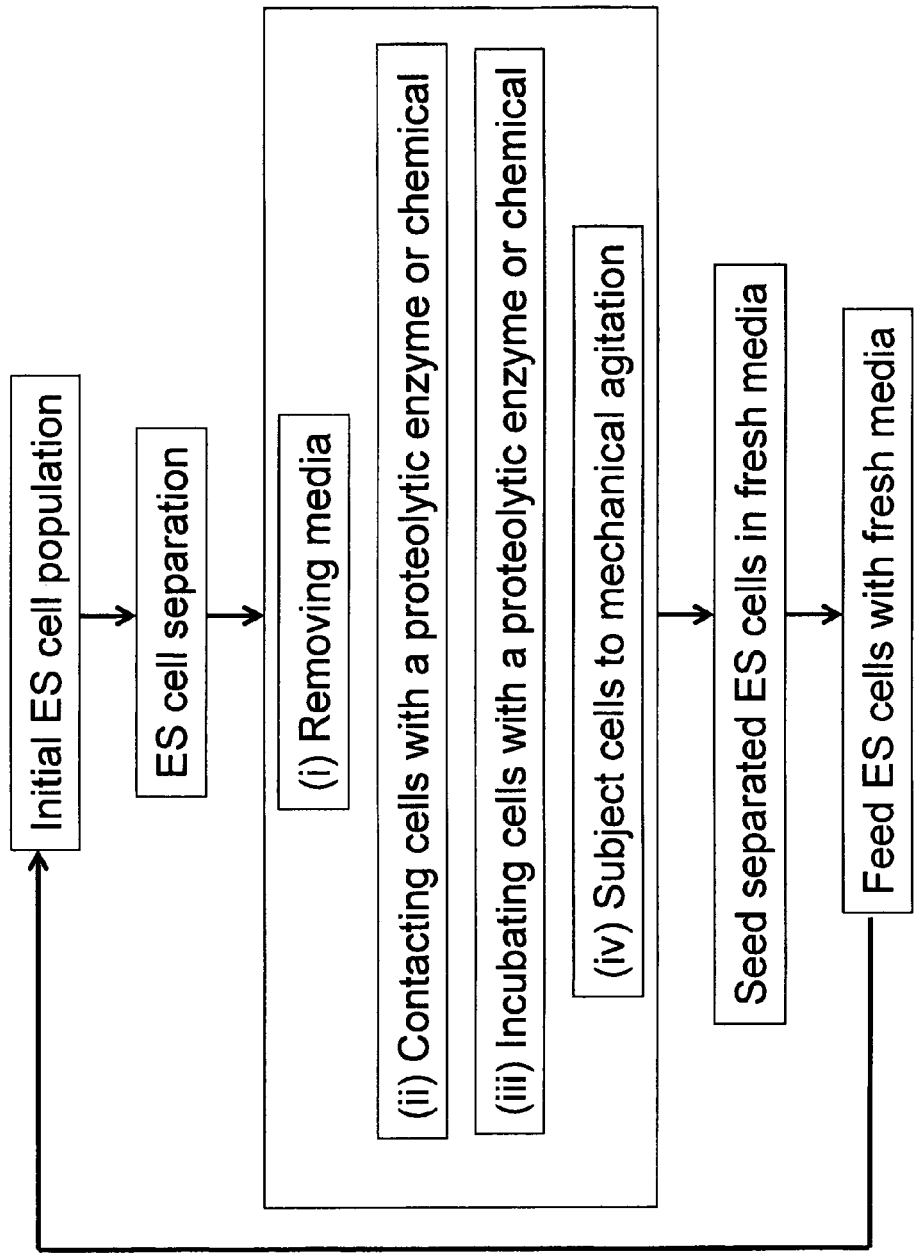
FIG. 1: An example automated method of embryonic stem expansion. One or more of the depicted steps may be comprised in a program to control a system for stem cell expansion.

Human stem cells are currently being developed for use in a variety of therapeutic and diagnostic applications. In particular, ESCs maybe differentiated into a variety of cell types and thus may be used to treat or study disease of a variety of human tissues. However, availability of large numbers of cultured human stem cells has proven to be a major limitation in the field. Unlike conventional tissue culture of transformed cell lines, ESCs are very sensitive to growth conditions and the surrounding microenvironment can modulate the cell viability and the speed at which ESCs proliferate. Furthermore, ESC culture is very human labor intensive thereby increasing the cost of expanding cell populations and increasing the probability of contamination of cell cultures. Even these laborious methods of cell culture have typically only enabled about a 1:12 expansion ratio, thereby limiting the number of cells that could be grown over a particular period of time and increasing the frequency of cell splitting required to maintain maximal cell proliferation rates.

The instant invention addresses many of the deficiencies of previous methods for ESC culture in providing an automated method for passaging and expanding ESC cell cultures. As shown in the below examples, an apparatus and system was produced which allowed for the automated feeding and splitting of ES cells which allowed for the expansion of one well of a 6-well plate of HES cells (~2.5 million cells) to a final number of 160 plates (~2-3 billion cells). This is the equivalent to a 1000-fold expansion over 3 weeks, an otherwise nearly impossible task for a single person. As shown by Oct4 staining, the vast majority of these stem cells, i.e., greater than 97%, remained in an undifferentiated state.

The instant invention provided an automated ESC culture system that employs a limited enzymatic treatment of cell clusters to separate the cells for seeding on new plates. Thus, in some aspects mechanical agitation of cell cultures is limited and a larger portion of viable ESCs are carried for passage to passage. In particular, methods and compositions provided herein enabled cells to be expanded from one plate to 30 plates (i.e., to a 30× greater surface area) in a single split, which is an improvement over hand-splitting methods, which typically allow for no more than 12-fold expansion at any given time. Furthermore, automated systems described here greatly reduce the need for human labor and thus the cost of culturing cells. Such automated apparatus and systems may be less prone to contamination and are preferred for stem cell products that may be ultimately used as therapeutics. Thus, the instant invention may enable rapid commercial development of ESC therapeutics such as, e.g., ESC derived blood for use in transfusion.

I. Cell Growth Media

A variety of media an culture conditions for ES cell culture are known in the art. In certain aspects, cells may be grown with feeder cells such a fibroblasts or in fibroblast conditioned media. However, in some instances it may be preferred that ES cells are grown in the absence of feeder cells. In still more preferred aspects cells may be grown in a defined media such as TeSR (e.g., MTESR™1 available from BD Biosciences) (Ludwig et al., 2006a, U.S. Application 2006/0084168). Such media may be used for serum free culture of ES cells. For example, in some cases growth media may be the media defined in Table 1. However, due to the high cost of serum free systems in certain cases growth factors used for serum free culture may be obtained from alternate sources to reduce cost, such a FGF cloned from zebra fish as described by Ludwig et al. (2006b). Furthermore, in certain aspects, media is supplemented with bovine or human serum to supply the necessary growth factors (Ludwig et al., 2006b). Thus, in certain cases, an ES growth media may comprise the ingredients as shown in Table 1, wherein the media is supplemented with bovine serum in place of the indicated "growth factors and proteins," as exemplified herein.

TABLE 1

| Formulation for TeSR1 Medium | |
|---|---|
| | mM |
| INORGANIC SALTS | |
| Calcium chloride (Anhydrous) | 8.24E−01 |
| HEPES | 1.18E+01 |
| Lithium Chloride (LiCl) | 9.80E−01 |
| Magnesium chloride (Anhydrous) | 2.37E−01 |
| Magnesium Sulfate ($MgSO_4$) | 3.19E−01 |

TABLE 1-continued

Formulation for TeSR1 Medium

| | mM |
|---|---|
| Potassium chloride (KCl) | 3.26E+00 |
| Sodium bicarbonate (NaHCO$_3$) | 1.80E+01 |
| Sodium chloride (NaCl) | 9.46E+01 |
| Sodium phosphate, dibas (Anhydrous) | 3.92E-01 |
| Sodium phosphate, mono. (NaH$_2$PO$_4$—H20) | 3.55E-01 |
| TRACE MINERALS | |
| Ferric Nitrate (Fe(NO$_3$)$_3$—9H$_2$O) | 9.71E-05 |
| Ferric sulfate (FeSO$_4$—7H$_2$O) | 1.18E-03 |
| Cupric sulfate (CuSO$_4$—5H$_2$O) | 4.08E-06 |
| Zinc sulfate (ZnSO$_4$—7H$_2$O) | 1.18E-03 |
| Ammonium Metavanadate NH$_4$VO$_3$ | 1.09E-05 |
| Mangenous Sulfate Mn SO$_4$ H$_2$O | 1.97E-06 |
| NiSO$_4$ 6H$_2$O | 9.70E-07 |
| Selenium | 1.77E-04 |
| Sodium Meta Silicate Na$_2$SiO$_3$ 9H$_2$O | 9.66E-04 |
| SnCl$_2$ | 1.24E-06 |
| Molybdic Acid, Ammonium salt | 1.97E-06 |
| CdCl$_2$ | 1.22E-05 |
| CrCl$_3$ | 1.98E-06 |
| AgNO$_3$ | 9.81E-07 |
| AlCl$_3$ 6H$_2$O | 4.87E-06 |
| Ba (C$_2$H$_3$O$_2$)$_2$ | 9.79E-06 |
| CoCl$_2$ 6H$_2$O | 9.81E-06 |
| GeO$_2$ | 4.97E-06 |
| KBr | 9.89E-07 |
| KI | 1.00E-06 |
| NaF | 9.83E-05 |
| RbCl | 9.81E-06 |
| ZrOCl$_2$ 8H$_2$O | 9.80E-06 |
| ENERGY SUBSTRATES | |
| D-Glucose | 1.37E+01 |
| Sodium Pyruvate | 3.92E-01 |
| LIPIDS | |
| Linoleic Acid | 1.88E-04 |
| Lipoic Acid | 4.00E-04 |
| Arachidonic Acid | 1.29E-05 |
| Cholesterol | 1.12E-03 |
| DL-alpha tocopherol-acetate | 2.90E-04 |
| Linolenic Acid | 6.99E-05 |
| Myristic Acid | 8.59E-05 |
| Oleic Acid | 6.94E-05 |
| Palmitic Acid | 7.65E-05 |
| Palmitoleic acid | 7.71E-05 |
| Stearic Acid | 6.89E-05 |
| AMINO ACIDS | |
| L-Alanine | 1.37E-01 |
| L-Arginine hydrochloride | 5.48E-01 |
| L-Asparagine-H$_2$O | 1.37E-01 |
| L-Aspartic acid | 1.37E-01 |
| L-Cysteine-HCl—H$_2$O | 7.83E-02 |
| L-Cystine 2HCl | 7.83E-02 |
| L-Glutamic acid | 1.37E-01 |
| L-Glutamine | 2.94E+00 |
| Glycine | 2.94E-01 |
| L-Histidine-HCl—H$_2$O | 1.18E-01 |
| L-Isoleucine | 3.26E-01 |
| L-Leucine | 3.54E-01 |
| L-Lysine hydrochloride | 3.91E-01 |
| L-Methionine | 9.06E-02 |
| L-Phenylalanine | 1.69E-01 |
| L-Proline | 2.16E-01 |
| L-Serine | 2.94E-01 |
| L-Threonine | 3.52E-01 |
| L-Tryptophan | 3.46E-02 |
| L-Tyrosine 2Na 2H$_2$O | 1.68E-01 |
| L-Valine | 3.55E-01 |
| VITAMINS | |
| Ascorbic acid | 2.53E-01 |
| Biotin | 1.12E-05 |
| B12 | 3.94E-04 |

TABLE 1-continued

Formulation for TeSR1 Medium

| | mM |
|---|---|
| Choline chloride | 5.03E-02 |
| D-Calcium pantothenate | 3.69E-03 |
| Folic acid | 4.71E-03 |
| i-Inositol | 5.49E-02 |
| Niacinamide | 1.30E-02 |
| Pyridoxine hydrochloride | 7.62E-03 |
| Riboflavin | 4.56E-04 |
| Thiamine hydrochloride | 2.42E-02 |
| GROWTH FACTORS/PROTEINS | |
| GABA | 9.79E-01 |
| Pipecolic Acid | 9.84E-04 |
| bFGF | 5.77E-06 |
| TGF beta 1 | 2.35E-08 |
| Human Insulin | 3.92E-03 |
| Human Holo-Transferrin | 1.37E-04 |
| Human Serum Albumin | 1.95E-01 |
| Glutathione (reduced) | 6.38E-03 |
| OTHER COMPONENTS | |
| Hypoxanthine Na | 1.18E-02 |
| Phenol red | 1.69E-02 |
| Putrescine-2HCl | 3.95E-04 |
| Thymidine | 1.18E-03 |
| 2-mercaptoethanol | 9.80E-02 |
| Pluronic | F-68 2.33E-02 |
| Tween 80 | 3.29E-04 |

A. ROCK Inhibitors

In still further aspects of the invention additional media components may be included in ES cell growth media such as molecules that reduce ES cell apoptosis when cells become disassociated (e.g., during splitting of cell populations). For example, media for use in the invention may comprise one or more Rho-associated kinase (ROCK) inhibitor such a Y-27632 or a derivative thereof. Furthermore, in some aspects, media of the invention may comprise HA-100: or a derivative thereof.

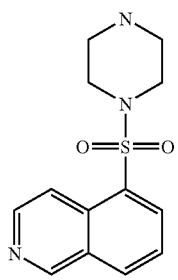

HA-100

The HA-100 may be present in an ES cell growth media, e.g., at a concentration of about 1-15 µM, 5-15 µM, 1-30 µM, 5-30 µM, or about 5, 6, 7, 8, 9, 10, 11, 12, 13, 14, 15, 16, 17, 18, 19, 20, 21, 22, 23, 24, 25, 26, 27, 28, 29, or 30 µM, or any range derivable therein. In certain embodiments HA-100 is present in an ES cell growth media at about 10-20 µM.

Other ROCK inhibitors which may be included in an ES cell growth media according to the present invention include H-1152 ((S)-(+)-2-Methyl-1-[(4-methyl-5-isoquinolinyl)sulfonyl]homopiperazine). H-1152 exhibits an approximately ten-fold greater potency than HA-100. Thus, H-1152 may be present in an ES cell growth media, e.g., at a concentration of about 0.1-10 µM, about 0.5-5 µM, about 1-3 µM, or about 0.5, 0.6, 0.7, 0.8, 0.9, 1, 2, 3, 4, or 5 µM, or any range derivable therein. In certain embodiments HA-100 is present in an ES cell growth media at about 1 μM. H-1152, which allows for very efficient seeding of individualized human ES cells in 96-well plates (similar to HA-100 but at 10-fold lower concentration). Individualized HES cells that are otherwise passaged in cell clumps allow more uniform cell densities per well, which is a stringent prerequisite for cell-based small molecule screening. H-1152 can thus be used in protocols for ES cell-based small molecule screening which involve automated cell culture according to the present invention. H-1152 has been previously described in, e.g., Ikenoya et al. (2002) and Sasaki et al. (2002), which are incorporated herein by reference.

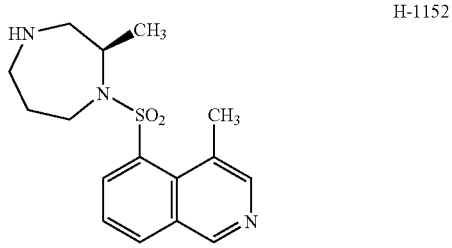 [SMILES: Cc1cncc2cccc(S(=O)(=O)N3CCCNC[C@H]3C)c12]

H-1152

Other ROCK inhibitors which may be included in an ES cell growth media include Y-27632, N-(4-Pyridyl)-N'-(2,4,6-trichlorophenyl)urea, 3-(4-Pyridyl)-1H-indole, glycyl-H1152 ((S)-(+)-2-Methyl-4-glycyl-1-(4-methylisoquinolinyl-5-sulfonyl)homopiperazine) and/or HA1100 (Hydroxyfausdil). Y-27632 ((R)-(+)-trans-4-(1-Aminoethyl)-N-(4-Pyridyl)cyclohexanecarboxamide) is commercially available from Sigma-Aldrich and has been described previously (see, e.g., Maekawa et al., 1999; Davies et al., 2000).

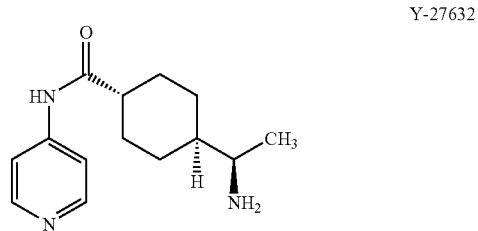 [SMILES: C[C@@H](N)[C@H]1CC[C@H](C(=O)Nc2ccncc2)CC1]

Y-27632

II. Cell Culture Apparatus, Systems and Methods

In some aspects, the present invention may take advantage of bioreactor technology. Growing cells according to the present invention in a bioreactor allows for large scale production of fully biologically-active cells capable of further differentiation for end use. Bioreactors have been widely used for the production of biological products from both suspension and anchorage dependent animal cell cultures. Microcarrier cell culture in stirred tank bioreactor provides very high volume-specific culture surface area and has been used for the production of viral vaccines (Griffiths, 1986). Furthermore, stirred tank bioreactors have industrially been proven to be scaleable, however such technologies may only be employed when cells may be grown in anchorage independent cultures. The multiplate CELLCUBE™ cell culture system manufactured by Corning-Costar also offers a very high volume-specific culture surface area. Cells grow on both sides of the culture plates hermetically sealed together in the shape of a compact cube. Unlike stirred tank bioreactors, the CELLCUBE™ culture unit is disposable. This is very desirable at the early stage production of clinical product because of the reduced capital expenditure, quality control and quality assurance costs associated with disposable systems.

A. Non-Perfused Attachment Systems

Traditionally, anchorage-dependent cell cultures are propagated on the bottom of small glass or plastic vessels as described herein. The restricted surface-to-volume ratio offered by classical and traditional techniques, suitable for the laboratory scale, has created a bottleneck in the production of cells and cell products on a large scale. In an attempt to provide systems that offer large accessible surfaces for cell growth in small culture volume, a number of techniques have been proposed: the roller bottle system, the stack plates propagator, the spiral film bottle system, the hollow fiber system, the packed bed, the plate exchanger system, and the membrane tubing reel. Since these systems are non-homogeneous in their nature, and are sometimes based on multiple processes, they suffer from the following shortcomings—limited potential for scale-up, difficulties in taking cell samples, limited potential for measuring and controlling key process parameters and difficulty in maintaining homogeneous environmental conditions throughout the culture.

Despite these drawbacks, a commonly used process for large scale anchorage-dependent cell production is the roller bottle. Being little more than a large, differently shaped T-flask, simplicity of the system makes it very dependable and, hence, attractive. Fully automated robots are available that can handle thousands of roller bottles per day, thus eliminating the risk of contamination and inconsistency associated with the otherwise required intense human handling.

B. Cultures on Microcarriers

In an effort to overcome the shortcomings of the traditional anchorage-dependent culture processes, van Wezel (1967) developed the concept of the microcarrier culturing systems. In this system, cells are propagated on the surface of small solid particles suspended in the growth medium by slow agitation. Cells attach to the microcarriers and grow gradually to confluency on the microcarrier surface. In fact, this large scale culture system upgrades the attachment dependent culture from a single disc process to a unit process in which both monolayer and suspension culture have been brought together. Thus, combining the necessary surface for a cell to grow with the advantages of the homogeneous suspension culture increases production.

The advantages of microcarrier cultures over most other anchorage-dependent, large-scale cultivation methods are several fold. First, microcarrier cultures offer a high surface-to-volume ratio (variable by changing the carrier concentration) which leads to high cell density yields and a potential for obtaining highly concentrated cell products. Cell yields are up to $1\text{-}2\times10^7$ cells/ml when cultures are propagated in a perfused reactor mode. Second, cells can be propagated in one unit process vessels instead of using many small low-productivity vessels (i.e., flasks or dishes). This results in far better nutrient utilization and a considerable saving of culture medium. Moreover, propagation in a single reactor leads to reduction in need for facility space and in the number of handling steps required per cell, thus reducing labor cost and risk of contamination. Third, the well-mixed and homogeneous microcarrier suspension culture makes it possible to monitor and control environmental conditions (e.g., pH, $pO_2$, and concentration of medium components), thus leading to more reproducible cell propagation and product recovery. Fourth, it is possible to take a representative sample for microscopic observation, chemical testing, or enumeration. Fifth, since microcarriers settle out of suspension quickly, use of a fed-batch process or harvesting of cells can be done relatively easily. Sixth, the mode of the anchorage-dependent culture propagation on the microcarriers makes it possible to use this system for other cellular manipulations, such as cell transfer without the use of proteolytic enzymes, cocultivation of cells, transplantation into animals, and perfusion of the culture using decanters, columns, fluidized beds, or hollow fibers for microcarrier retainment. Seventh, microcarrier cultures are relatively easily scaled up using conventional equipment used for cultivation of microbial and animal cells in suspension.

C. Microencapsulation of Mammalian Cells

One method which has shown to be particularly useful for culturing mammalian cells is microencapsulation. The mammalian cells are retained inside a semipermeable hydrogel membrane. A porous membrane is formed around the cells permitting the exchange of nutrients, gases, and metabolic products with the bulk medium surrounding the capsule. Several methods have been developed that are gentle, rapid and non-toxic and where the resulting membrane is sufficiently porous and strong to sustain the growing cell mass throughout the term of the culture. These methods are all based on soluble alginate gelled by droplet contact with a calcium-containing solution. Lim (1982, U.S. Pat. No. 4,352,883, incorporated herein by reference) describes cells concentrated in an approximately 1% solution of sodium alginate which are forced through a small orifice, forming droplets, and breaking free into an approximately 1% calcium chloride solution. The droplets are then cast in a layer of polyamino acid that ionically bonds to the surface alginate. Finally the alginate is reliquefied by treating the droplet in a chelating agent to remove the calcium ions. Other methods use cells in a calcium solution to be dropped into a alginate solution, thus creating a hollow alginate sphere. A similar approach involves cells in a chitosan solution dropped into alginate, also creating hollow spheres.

Microencapsulated cells are easily propagated in stirred tank reactors and, with beads sizes in the range of 150-1500 µm in diameter, are easily retained in a perfused reactor using a fine-meshed screen. The ratio of capsule volume to total media volume can be maintained from as dense as 1:2 to 1:10. With intracapsular cell densities of up to $10^8$, the effective cell density in the culture is $1\text{-}5 \times 10^7$.

The advantages of microencapsulation over other processes include the protection from the deleterious effects of shear stresses which occur from sparging and agitation, the ability to easily retain beads for the purpose of using perfused systems, scale up is relatively straightforward and the ability to use the beads for implantation.

D. Perfused Attachment Systems

Perfused attachment systems are a preferred form of the present invention. Perfusion refers to continuous flow at a steady rate, through or over a population of cells (of a physiological nutrient solution). It implies the retention of the cells within the culture unit as opposed to continuous-flow culture which washes the cells out with the withdrawn media (e.g., chemostat). The idea of perfusion has been known since the beginning of the century, and has been applied to keep small pieces of tissue viable for extended microscopic observation. The technique was initiated to mimic the cells milieu in vivo where cells are continuously supplied with blood, lymph, or other body fluids. Without perfusion, cells in culture go through alternating phases of being fed and starved, thus limiting full expression of their growth and metabolic potential.

The current use of perfused culture is in response to the challenge of growing cells at high densities (i.e., $0.1\text{-}5 \times 10^8$ cells/ml). In order to increase densities beyond $2\text{-}4 \times 10^6$ cells/ml, the medium has to be constantly replaced with a fresh supply in order to make up for nutritional deficiencies and to remove toxic products. Perfusion allows for a far better control of the culture environment (pH, $pO_2$, nutrient levels, etc.) and is a means of significantly increasing the utilization of the surface area within a culture for cell attachment.

The development of a perfused packed-bed reactor using a bed matrix of a non-woven fabric has provided a means for maintaining a perfusion culture at densities exceeding $10^8$ cells/ml of the bed volume (CELLIGEN™, New Brunswick Scientific, Edison, N.J.; Wang et al., 1992; Wang et al., 1993; Wang et al., 1994). Briefly described, this reactor comprises an improved reactor for culturing of both anchorage- and non-anchorage-dependent cells. The reactor is designed as a packed bed with a means to provide internal recirculation. Preferably, a fiber matrix carrier is placed in a basket within the reactor vessel. A top and bottom portion of the basket has holes, allowing the medium to flow through the basket. A specially designed impeller provides recirculation of the medium through the space occupied by the fiber matrix for assuring a uniform supply of nutrient and the removal of wastes. This simultaneously assures that a negligible amount of the total cell mass is suspended in the medium. The combination of the basket and the recirculation also provides a bubble-free flow of oxygenated medium through the fiber matrix. The fiber matrix is a non-woven fabric having a "pore" diameter of from 10 µm to 100 µm, providing for a high internal volume with pore volumes corresponding to 1 to 20 times the volumes of individual cells.

In comparison to other culturing systems, this approach offers several significant advantages. With a fiber matrix carrier, the cells are protected against mechanical stress from agitation and foaming. The free medium flow through the basket provides the cells with optimum regulated levels of oxygen, pH, and nutrients. Products can be continuously removed from the culture and the harvested products are free of cells and can be produced in low-protein medium which facilitates subsequent purification steps. Also, the unique design of this reactor system offers an easier way to scale up the reactor. Currently, sizes up to 30 liter are available. One hundred liter and 300 liter versions are in development and theoretical calculations support up to a 1000 liter reactor. This technology is explained in detail in WO 94/17178 (Aug. 4, 1994, Freedman et al.), which is hereby incorporated by reference in its entirety.

The CELLCUBE™ (Corning-Costar) module provides a large styrenic surface area for the immobilization and growth of substrate attached cells. It is an integrally encapsulated sterile single-use device that has a series of parallel culture plate joined to create thin sealed laminar flow spaces between adjacent plates.

The CELLCUBE™ module has inlet and outlet ports that are diagonally opposite each other and help regulate the flow of media. During the first few days of growth the culture is generally satisfied by the media contained within the system after initial seeding. The amount of time between the initial seeding and the start of the media perfusion is dependent on the density of cells in the seeding inoculum and the cell growth rate. The measurement of nutrient concentration in the circulating media is a good indicator of the status of the culture. When establishing a procedure it may be necessary to monitor the nutrients composition at a variety of different perfusion rates to determine the most economical and productive operating parameters.

Cells within the system reach a higher density of solution (cells/ml) than in traditional culture systems. Many typically used basal media are designed to support 1-2×10$^6$ cells/ml/day. A typical CELLCUBE™, run with an 85,000 cm$^2$ surface, contains approximately 6 L media within the module. The cell density often exceeds 10$^7$ cells/mL in the culture vessel. At confluence, 2-4 reactor volumes of media are required per day.

III. Apparatus/Systems for Automated Expansion of ES Cells

Figure 2A:
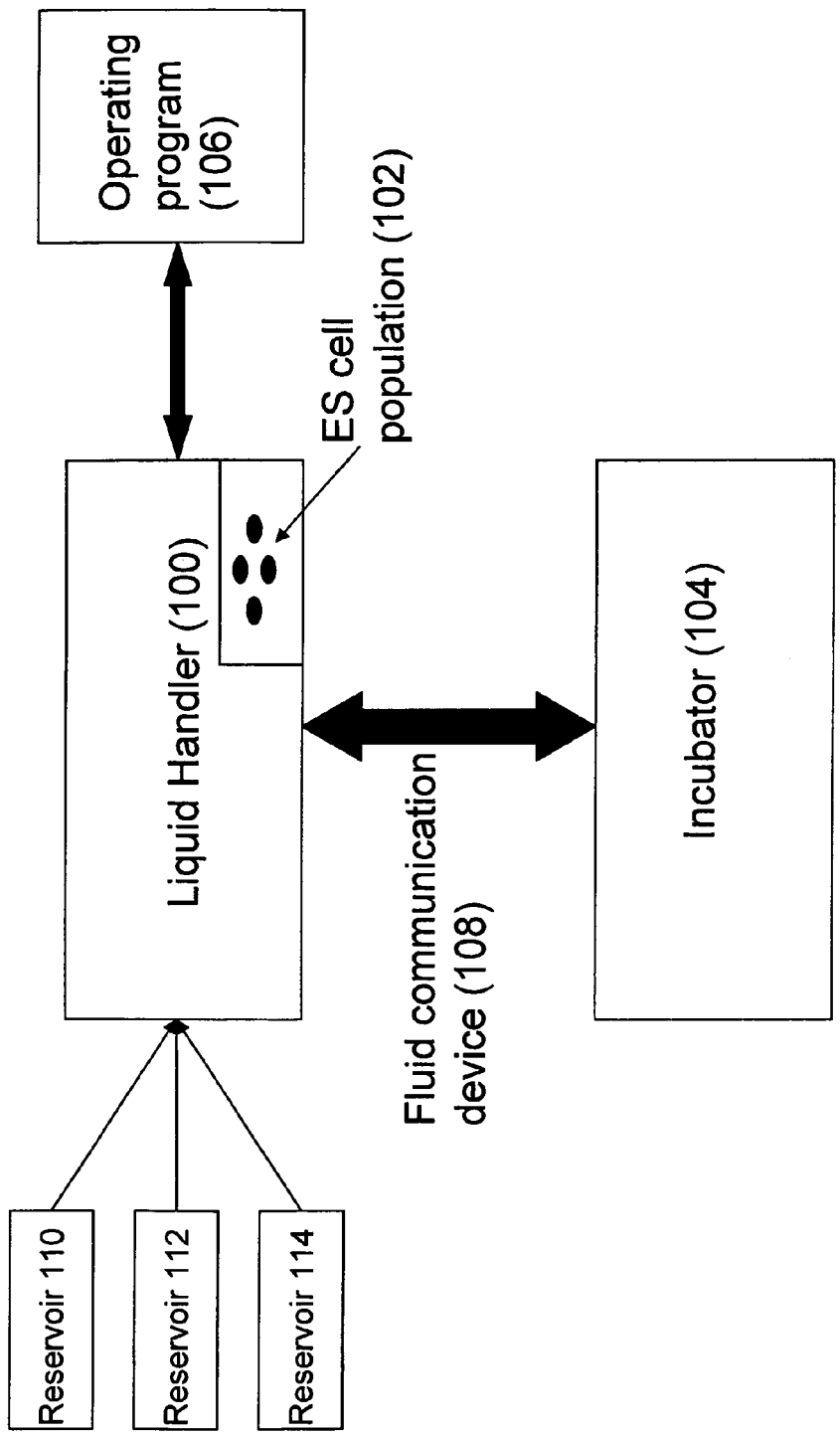
FIGS. 2A-B: Diagrams of exemplary apparatus and systems for automated expansion of ES cells.
Figure 2B:
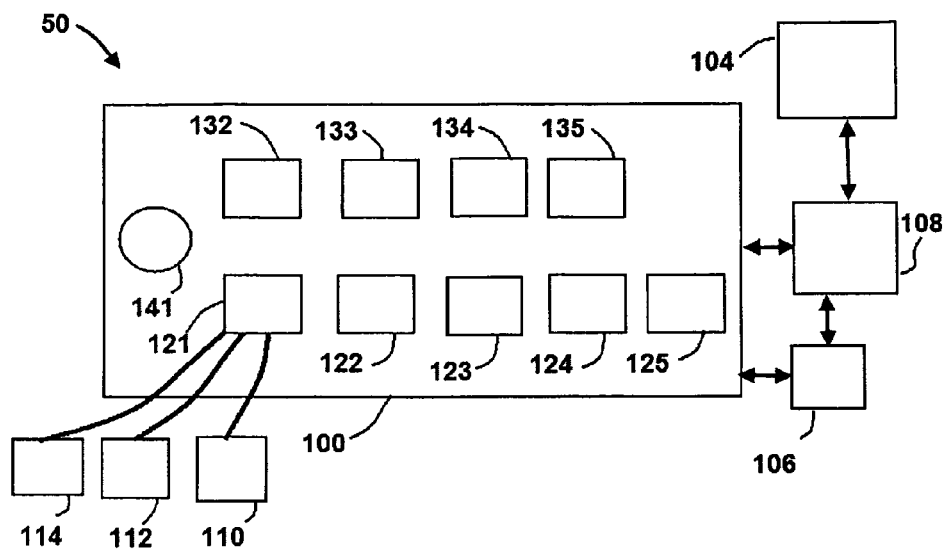

Certain aspects of the invention concern apparatus or systems for automated expansion of pluripotent cells, such as ES cells, depicted in diagram form in FIGS. 2A and 2B, and illustrated with commonly available hardware elements in FIGS. 3A-D. Thus, as can be seen, an exemplary device can comprise a viable ES cell population (102), a liquid handler unit (100) in fluid communication with an incubator (104) and a controller (106) comprising an operating program for cell separation.

ES cell populations (102) for use in an apparatus of the invention may comprise an ES cell population from any source known to those of skill in the art. For instance, methods for obtaining embryonic stem cells, such as human ESCs have been previously described in U.S. Pat. Nos. 5,843,780, 6,200,806 and 7,029,913. It is understood that the term apparatus as used herein is not limited to devices in a single housing, and may include multiple devices linked together, for example, via electrical, mechanical, or other coupling mechanisms.

Various types of liquid handler units (100) are commercially available, for example in certain aspects, a liquid handler may be a robotic handler such as a Hamilton MICROLAB® STAR work station or a Beckman Coulter BIOMEK® 2000 liquid handler (B2K). See also, U.S. Pat. No. 6,325,114 concerning robotic liquid handlers. In still other aspects, a liquid handler maybe a device that does not comprise a robotic arm but rather moves liquid by actuation of valves and the application of pressure gradients, such as a fluidic or microfluidic liquid handler.

A wide array of incubators (104) are known in the art and may be used according to embodiments of the invention. For example, in certain embodiments an incubator may be a Kendro CYTOMAT™ incubator.

Furthermore, pluripotent or ES cell expansion apparatus and systems in certain embodiments of the invention may comprise a controller (106) for the control of ES cell expansion. Such a program may be in electronic communication with liquid handler unit (100), a fluid communication device (108) and/or an incubator (104). The skilled artisan will recognize that in certain aspects, an operating apparatus or system may be comprised in a computer or a computer-readable medium. An example operating program for use in embodiments of the invention may comprise the steps depicted in FIG. 1. In this exemplary embodiment, the operating controller directs ES cell separation, that is effected by: (i) removing media; (ii) contacting cells of the ES cell population with a proteolytic chemical or enzyme such as trypsin; (iii) incubating and agitating the cells to ensure disassociation of the cells; and (iv) seeding the separated ES cells in fresh media. In certain embodiments, the above-described process can be repeated to produce additional ES cells.

As will be appreciated, the operating apparatus may be effected by means of computer automation, whereby the operating apparatus directs and controls the various hardware devices that make up certain embodiments of the present invention. An exemplary operating program that may be employed to effect integration of hardware elements is the OVERLORD™ Integration software program (Biosero, Inc.), which employs a simple drag-and-drop system for setting up communication between instruments. The software also permits a range of programming elements such as numeric and string variables, conditional statements (e.g., IF THEN, ELSE), and control loops (e.g., FORNEXT).

Optionally, an apparatus according to the invention may comprise fluid communication device (108) that facilitates fluid communication between incubator (104) and liquid handler unit (100). For example, in the case where a liquid handler is a robotic handler, fluid communication device (108) may be a robotic device, such as a device that moves plates of cells between a liquid handler unit and an incubator. For example, a robotic device may be a Hudson Platecrane XL.

Furthermore, a pluripotent or ES cell expansion system may comprise one or more reservoirs (110, 112, 114) that comprise reagent for the liquid handler unit (100). For example, reservoirs may comprise: cell growth media (e.g., media comprising a ROCK inhibitor) with or without a proteinase inhibitor; cell culture plates; a proteolytic enzyme solution; phosphate buffered saline (PBS); and/or pipette tips. In certain aspects, additional robotic devices may be used to facilitate communication between a liquid handler device and a reservoir. In certain embodiments a reservoir may contain a TeSR media, optionally with a ROCK inhibitor and/or a protease inhibitor such as a soybean trypsin inhibitor. In other embodiments, the reservoir may contain a solution comprising a proteolytic enzyme (e.g., trypsin, EDTA, etc.), For example, in some aspects a Beckman Coulter Stacker Carousel may be used to facilitate communication between a reservoir (e.g., a plate or pipette reservoir) and a liquid handler device. The reservoirs may be housed in a temperature control unit, such as a refrigerator. The temperature control unit may optionally comprise a heating unit to pre-heat solutions to a desired temperature (e.g., about 37° C.); however, the inventors have discovered that a heating unit is not necessary in certain embodiments, as a simple refrigerator has been successfully used in the below examples.

Referring now to FIG. 2B, a top view of an apparatus 50 for providing automated cell culture comprises a stacker carousel (141), a liquid handler unit (100), an incubator (104), a fluid communication device (108), a controller (106), and a series of reservoirs (110, 112, 114). In certain embodiments, the stacker carousel (141) is mechanically coupled to or comprises part of the liquid handler unit (100). As used herein, the term "reservoir" includes any device capable of retaining a volume of fluid. It is also understood that various components shown in FIG. 2B can be combined or separated. For example, reservoirs (110, 112, 114) can be integral with liquid handler unit (100), or separate from liquid handler unit (100). In specific embodiments, fluid communication device (108) is a robotic arm, e.g. a Hudson Platecrane XT. In certain embodiments, liquid handler unit (100) is a Biomek2000 and incubator 400 is a Cytomat6000 model.

In the illustrated embodiment, liquid handler unit (100) further comprises a tool station 121 that comprises various sizes of liquid handling tools, e.g. pipetting tools that can be used to pipette different volumes of liquid. Tool station (121) can also comprise a gripper tool that can be used, e.g. to remove and/or install lids from cell culture plates during various steps of the cell culture process. In the specific embodiment shown, liquid handler unit (100) comprises a station (122) that includes P250 barrier tips, which can be used with MP200 pipette tools of station (121). In addition, liquid handler unit (100) comprises a station (123) for source plates, a station (124) for lids for daughter plates, and a station (125) for daughter plates.

In the embodiment shown in FIG. 2B, liquid handler unit (100) also comprises a station (132) that serves as a proteolytic enzyme (e.g., trypsin solution) or chemical reservoir, a station (133) that provides lids for source plates, a station (134) that provides lids for daughter plates, and a station (135) that provides daughter plates.

In certain embodiments, automated passaging may be accomplished using the following exemplary protocol: After retrieval of a mother plate from incubator (104) via fluid communication device (108), a wash tool from station (121) removes the spent media. A pipetting tool (e.g., an 8-channel 200 µl pipetting tool MP200) from station (121) can then add about 3 ml of trypsin (0.1%) from station (132). Fluid communication device can then transfer the plate to incubator 104. After an incubation of about 7 minutes, fluid communication device (108) transfers the treated plate back to liquid handler unit (100). A mixture of 3 ml TeSR medium containing 2 µM H-1152 and 1 mg/ml Invitrogen Soybean Trypsin Inhibitor is then added to each well from one or more of reservoirs (110, 112, 114). The cells can then be washed off the plate surface and mixed using a pipetting tool from station 121 by repetitive dispensing and aspiration. The cells can then be dispensed to daughter plates provided from station 125 or 135 using the pipetting tool from station 121.

The cells can then be seeded at a ratio of, e.g., 1:32 onto precoated Matrigel plates loaded from the stacker carousel (131) to the liquid handler (100) (e.g., Biomek2000). Seeding can be done after aspirating the Matrigel coating media and replacing it with a modified TeSR media containing H-1152 and soybean inhibitor (e.g., TeSR containing 1 µM HA-1152 and 0.5 mg/ml Invitrogen Soybean Trypsin Inhibitor) provided from one or more of reservoirs (110, 112, 114). Controller (106) may be used to control the movements of liquid handler unit (100), fluid communication device (108), and/or incubator (104). A gripper tool from station 121 may also be used to remove or install lids from plates during appropriate steps in the automated cell culture method.

As stated above, the H-1152 could be replaced with another ROCK inhibitor such as H-100 if desired. In this way, the cells may be separated and split without the need for physically of removing the proteolytic enzyme from the growth media; for example, using this approach, the inactivated trypsin does not need to be physically removed from the media, e.g., via centrifugation.

In various embodiments, multiple robotic components may be utilized to further expedite the culturing protocol and increase the high throughput of the system. For example, multiple robotic arms may be utilized for a operating separate tools, and a liquid handling system like the Tecan Cellerity system, which has been successfully established for maintenance of other attached cell lines, may also be used with the present invention.

EXAMPLES

The following examples are included to further illustrate various aspects of the invention. It should be appreciated by those of skill in the art that the techniques disclosed in the examples that follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Automated Passage and Expansion of Stem Cells

H1 cells passage 185 and 62 were cultured using TeSR media and split using a Beckman Coulter Biomek 2000 liquid handler (B2K), Gibco TrypLE Trypsin, TeSR media and TeSR Plus (containing 10 µM HA-100 and 0.5 mg/ml Invitrogen Soybean Trypsin Inhibitor). H1 cells, approximately 70% confluent, were placed on the B2K work surface along with 6-well plates coated with 8.6 µg/cm$^2$ MATRIGEL™ (BD Bioscience) and a reservoir containing TRYPLE™ Trypsin. Using the Gripper tool, the lid from plate to be split was removed. The robot discarded the Gripper tool, and loaded the Wash1 tool to aspirate media from the plate with cells. Next, using the P1000 tool, TRYPLE™ enzyme was transferred to the plate to be split. The lid was replaced on the plate and the plate was moved into the 37° C. CYTOMAT™ incubator for 7 minutes to allow for cells to dissociate from plate.

During this time the lids from the MATRIGEL™ coated plate(s) were removed and excess MATRIGEL™ was removed using the Wash1 tool. The appropriate volume of TeSR Plus media was dispensed per well for each MATRIGEL™ coated plate. The plate from the incubator was then removed and uncovered using the Gripper tool. The Wash1 tool was used to add TeSR Plus media to the plate in order to neutralize the TRYPLE™ in the trypsinized well. Remaining clumps of cells were mixed slowly and broken up using the P1000 tool. The cell suspension was transferred to the new MATRIGEL™ coated plate(s), while intermittently mixing and slowly distributing (seeding) cells across the wells of each plate. This process was continued until all new plates were seeded with cells. Using the Gripper tool the lids were then placed back on plate(s), and plate(s) were placed at 37° C. degrees for 24 hours.

After 24 hours seeded plates were removed from incubator and using the Wash1 tool, TeSR plus media was aspirated and fresh regular TeSR media was added to each plate of cells. The lids were replaced and the plates were again placed back in incubator, and fed every 24 hours with regular TeSR media (TeSR without HA-100 and Soybean Trypsin Inhibitor) until they needed to be split again, approximately 4-5 days later. The method enabled cells to be expanded from one plate to 30 plates (i.e., to a 30× greater surface area) in a single split.

Example 2

Automated HES Cell Culture and Maintenance System

In order to improve labor and time-intensive maintenance of HES cells the inventors first automated feeding of HES cells. The proposed experiment was to maintain 10 6-well plates between passages by automated media exchange to establish sterile and reproducible conditions. The inventors achieved that goal by successfully automating media change using an established liquid handling system. This was an important step toward the automation of HES cell culture in this embodiment.

Figure 3A:
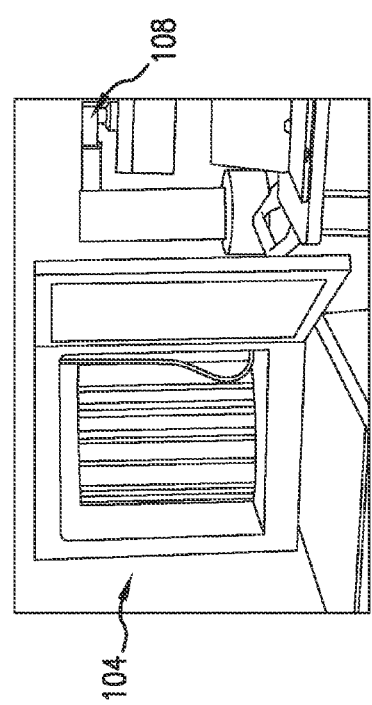
FIGS. 3A-B depict an example of an automated human ES (HES) culturing apparatus and system in a clean room.
Figure 3B:
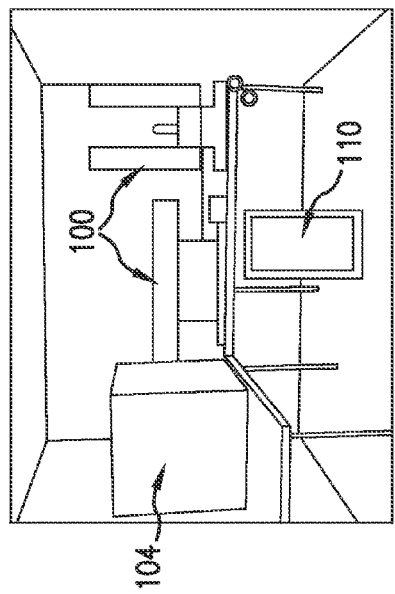
Figure 3C:
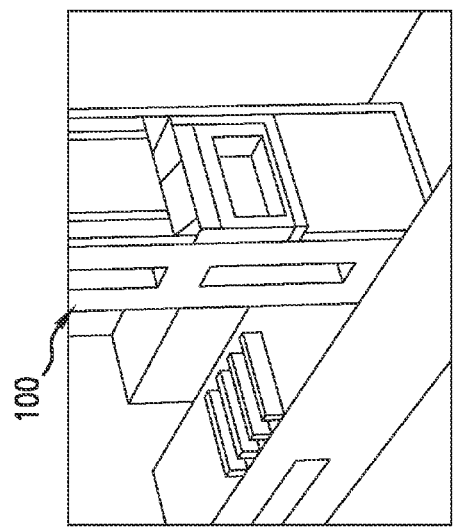
FIGS. 3C-D depict robotic components for splitting and feeding HES cells.
Figure 3D:
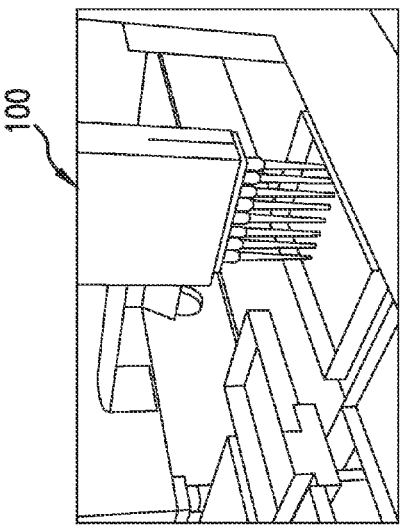

FIGS. 3A-B show the automated system used in the below experiments of exemplary embodiments. The system includes a Biomek2000 System (pin tools, wash tools, stacker, single and 8-channel 20, 200 and 1000 microliter pipetting tools (P20, P200, P1000, Beckman), a Hudson Platecrane XT, and a Heraeus Cytomat 6000. In this embodiment, a simple soda refrigerator was used for media storage from which the media was delivered directly to the culture wells. An in-line heating of the delivered media did not appear to be necessary based on experiments. The integration was done in collaboration with Biosero using Overlord software. The complete system was housed in a class 100 clean room (i.e. less than 100 particles larger than 0.5 microns per cubic feet) compliant with biosafety level 2 (BSL2, regulates handling of agents with moderate potential hazard to personnel and the environment) regulations and accomplished sufficient sterility comparable to a standard BSL2 tissue culture hood.

Rectangular 4-well and 8-well NunclonΔ plates purchased from Nunc were used instead of the round 6-well plates commonly used in manual procedures. One reason for this was that the plate height of all commercially available 6-well plates significantly exceeds those of regular microwell plates used in screening and automated liquid handling. The penalty of using regular round 6-well plates would have been a reduction of almost half of the capacity of the automated incubator to less than 100 plates. Furthermore, the rectangular geometry of the plates allowed the use of the 8-channel liquid handling tools since 6-well plates contain more inaccessible areas. The later fact also resulted in a 1.46-fold increase in usable culture surface area (84 cm2 for 4- and 8-well plates compared to 57.6 cm2 for a 6-well plate). The feeding and seeding system used 4-well and 8-well plates with the wash tool and the 8-channel tool (FIGS. 3 C-D).

In this embodiment, robotic components were used for splitting and feeding HES cells. The single channel wash tool was used initially to aspirate spent media and feed 4-well or 8 well plates. In the back behind the 4-well plate a 6-well plate is used to serve as a reservoir for trypsin. The 8-channel tool P200 was used to mix and dispense the trypsinized and individualized HES cells from a 4-well mother plate to an 8-well daughter plate in the final split.

In exemplary embodiments, the surface was NunclonΔ manufactured by Nunc and coated with Matrigel. The following robotic components can be used for splitting and feeding HES cells: the Platecrane connects the liquid handling robot Biomek2000 with the incubator Cytomat6000. The gripper of the Platecrane is positioned above the turntable of the Incubator. The refrigerator housing the media had tubing connecting the peristaltic pump of the wash tool (box with the tape) and the waste bottle for spent media coming from the vacuum was controlled by a valve in the wash tool which was provided by an in house vacuum system.

Initially, Omnitrays, i.e. plates with no divisions within the whole plate, were tested but were abandoned because of excessive splashing during transfers by the Platecrane and the turntable of the Cytomat6000. In the final feeding protocol (initially handled 6-well plates) two 8-well plates were retrieved from the Cytomat6000 one at a time and transferred to the two most outer right positions of the Biomek2000 deck using the Platecrane. The gripper tool of the Biomek2000 removed the lids from the plates and placed them on the adjacent left positions on the deck. After switching to the 8-channel wash tool the media is aspirated at 8 positions across the 4- or 8-well plate to insure sufficient removal of spent media. In the manual process the plate would be tipped at an angle to collect the spent media at the bottom for sufficient removal. Such an angle was not implemented with these robotics to maintain reliability. The new media (6 and 3 ml per well respectively) was dispensed immediately before moving on to the next well or plate. The delidding and relidding process as well as the height alignment of the wash tool required occasional intervention. These were the most prominent causes (about 1 in 100 movements) of errors that required operator presence and intervention. The flow rate of the wash tool did not seem to negatively affect the quality of the culture as the cells could not be washed off the surface by the pressure generated by the peristaltic pump of the wash tool. The quality of the culture was judged by visual assessment of the culture after each day of the culturing process (FIGS. 4A-C).

The automated procedure did not show any increased occurrence of differentiation during the 5 days of the experiment and the cultures could be successfully split manually onto regular Matrigel plates. Initial experiments with an in-line heating column to preheat the chilled media were not continued as the inventors did not observe any negative effect without the preheating column. The major and time-consuming task in this aim was to master the automated system for the key movements and operations that were similar during feeding and splitting. The throughput of this system for the step of feeding was somewhat limited due to: limitations including in the number of simultaneous movements possible by the integration software, the Biomek2000 being used to operate multiple tools (in the case of feeding: gripper and wash tool), and the configuration with the Platecrane and the available deck space of the Biomek2000 allowing simultaneous processing of two plates. However, a larger deck offered by more advanced liquid handling systems and a more sophisticated integration platform (multiple arms, compatible software, integratable robotics that allow multitasking) significant improvements in throughput can and have to be made. By the end of this study including aim 2 the inventors were able to demonstrate successfully that the inventors can maintain 160 NunclonΔ 8-well plates between passages by automated media exchange to establish sterile and reproducible conditions. A single person can routinely handle about 20 NunclonΔ 6-well plates per day without compromising culture quality. The above system clearly demonstrated good culture quality, measurable in maintenance of pluripotency (Oct4 levels), speed, reproducibility and economic efficiency of the HES cell culture comparable with manually maintained cell culturing techniques.

Example 3

Automated Passaging and Expansion of hES Cells

Since passaging of HES cells is the most labor intensive and variable step in HES cell culture it leads to tremendous variability in the outcome of experiments depending highly on the skills of the technician. The inventors hypothesized that automation of passaging will lead to more robust and reproducible HES cell culture. Although the inventors could not confirm this theory with the current system and due to the limited time available for this project, the inventors were able to demonstrate a proof of principle by expanding one well of a 6-well plate of HES cells (~2.5 million cells) to a final number of 160 plates (~2-3 billion cells) equivalent to a 1000-fold expansion over 3 weeks, an otherwise nearly impossible task for a single person.

The inventors utilized the system described in Example 1 and developed procedures for passaging of HES cells that were based on simple liquid handling protocols. Recent innovations in splitting techniques allowed for efficient automation of this otherwise demanding manual procedure. Since HES cells require cell-cell contacts for survival in TeSR media, they needed to be seeded in clumps which required scraping of attached cells, a procedure which would be very hard to automate. However, the small molecule HA-100 and its 10-fold more specific derivative H-1152 was determined to allow the survival of HES cells after trypsin treatment. The ability to detach and individualize HES cells with 0.1% trypsin and subsequent seeding onto Matrigel coated NunclonΔ plates in slightly modified defined TeSR medium containing 1 μM H-1152 and 0.5 mg/ml Invitrogen Soybean Trypsin Inhibitor allowed the inventors to adopt techniques that have been automated by others for less demanding adherent cancer cell lines.

For automated passaging, the following procedure was developed: After retrieval of the mother plate from the incubator, the wash tool removes the spent media as described in aim 1. The 8-channel 200 μl pipetting tool MP200 is used to add 3 ml of trypsin (0.1%). After 7 minute incubation of the treated plate inside the Cytomat6000, a mixture of 3 ml TeSR medium containing 2 μM H-1152 and 1 mg/ml Invitrogen Soybean Trypsin Inhibitor is added to the well. The cells are washed off the plate surface and mixed using the 8-channel MP200 tool by repetitive dispensing and aspiration. Cells are then dispensed to the daughter plates using the MP200 tool. The cells are then seeded 1 to 32 onto precoated Matrigel plates loaded from the stacker to the Biomek2000. Seeding is done after aspirating the Matrigel coating media and replacing it with the modified TeSR media containing H-1152 and soybean inhibitor as described in the feeding protocol above. The total surface area of the initially used Omnitray turned out to be too large for the throughput of the system at the stage of the next split once the inventors tested methods for passaging HES cells in aim 2. The time it took to distribute the cells from the mother plates to an average of 25 daughter plates exceeded the time the individualized cells could survive in suspension before they would be seeded.

The inventors used karyotypically normal very high passage (>p200) H1 HES cell cultures in the beginning to establish the robotic protocols with very robust growing cells to establish feasibility of these new protocols. These cells still produced hematopoietic precursors and cardiomyocytes to demonstrate their differentiation potential. However the demands for a robust protocol are certainly greater for lower passage cell cultures, since they react more sensitively to sub-optimal conditions, which leads to greater variability in cell culture. In later experiments, the inventors were able to confirm the validity of the derived procedures with lower passage H1 cells (>p60) in smaller scale experiments with 5 plates over 3 to 5 passages. This evidence supports the ability to culture these lower passage cells using the automated system.

Initially the inventors used the single channel tool for seeding by adding cells at multiple positions of the well to achieve homogeneous distribution of cells. Although the inventors could accomplish that successfully with high and low passage HES cultures, the throughput of the procedure required the use of the 8-channel P200 tool when the inventors expanded the cells in the final step of the scale-up experiment to 160 8-well plates. Although a reduced homogeneous distribution and decrease in cell densities of the cells was observed in the daughter plates, the inventors anticipate that this method may be optimized to improve these characteristics. The expansion in this experiment was done from a single well of a 6-well plate to 5 needed 4-well plates in the first passage and then into 160 final 8-well plates in the second passage. The inventors maintained all 160 plates by feeding 2 days after passage with the protocol established above and then every day. The inventors inspected all plates visually for differentiation and density. The inventors randomly picked 30 plates and stained them with trypan blue staining for scanning and evaluation of cell distribution. From the visual inspection of the plates it was apparent that further improvements can and should be made to homogeneity in the interest of high reproducibility. Also the inventors picked plate 2 and 10 randomly to test for Oct4 content of the cells after 2 passages and 1000-fold expansion over 20 days. Oct4 FACS analysis revealed a high quality of undifferentiated cells in this first scale-up experiment.

Figure 6:
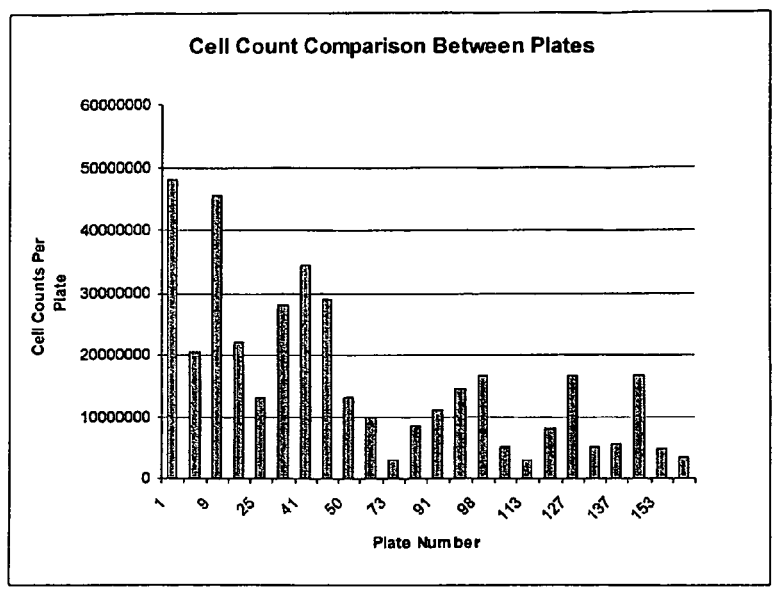
FIG. 6: Cell counts from randomly picked plates after 1000-fold expansion using the automated cell culture system. Plates were trypsinized and stained with trypan blue and counted on a hemacytometer. Total cells were calculated from representative samples. Extrapolated from the mean value indicates that approximately 160×16 million 2.56 billion human ES cells were generated.

No significant amount of differentiation was observed in any plate achieving a standard quality of automated HES cells culture. This was supported by many other experiments in smaller scale and with lower passage cultures as well as by the very high content of Oct4 positive cells in the FACS analysis. The passaging frequency and density to the current cell culture depended on its history and predominantly age (i.e. passage number). From experience with manual HES cell culture the inventors have learned that younger cultures have the tendency to react more sensitive to suboptimal conditions and harsh treatment than older cells. The behavior of a cell line can vary depending on how it is thawed and handled in the first few passages. All these factors can contribute to a large degree of variability that can only be harnessed by monitoring the growth and degree of differentiation. Such measures may be automated in subsequent variations of the system described here. As shown in FIG. 6, variability was observed amongst the plates. Improved mixing procedures and integrated cell-counting may accommodate better homogeneity in the future systems, these modifications should be relatively easily implemented since they have been accomplished with other cell cultures before.

Randomly picked plates from the scale-up experiment after 1000-fold expansion were examined. Plates were stained with trypan blue after media had been removed and the plates were dried. The dye marked the HES cell colonies. Although there remains a need for improved cell distribution when optimizing the splitting protocol, the inventors anticipate that improved consistency in the distribution across the plates can be achieved with optimization of the protocol.

Randomly picked plates from the scale-up experiment after 1000-fold expansion were subjected to cell counts. Plates were trypsinized and stained with trypan blue and counted on a hemacytometer. Total cells were calculated from representative samples. Extrapolated from the mean results shown in the below summary statistics, approximately 160× 16 million=2.56 billion cells were generated from the above experiments. Cell expansion in different plates are shown in FIG. 6, and the cell expansion summary statistics for this experiment are presented in Table 2 below.

TABLE 2

| Cell Expansion Results Summary Statistics | |
|---|---|
| Mean | 16023750 |
| Standard Error | 2615974.1 |
| Median | 13000000 |
| Mode | 16500000 |
| Standard Deviation | 12815603.45 |
| Sample Variance | 1.6424E+14 |
| Kurtosis | 0.987042208 |
| Skewness | 1.254713927 |
| Range | 44970000 |
| Minimum | 3000000 |
| Maximum | 47970000 |
| Sum | 384570000 |
| Count | 24 |

Example 4

Automated Seeding of HES Cell Culture for 96-Well Format for Cell-Based Screening The inventors used a new compound H1152 which actively increased colony formation of HES cells in TeSR1 media from individualized cells and represents a 2nd generation small molecule derived from HA-100. HA-100 was discovered in one of the first HES cell-based small molecule screens which led to the discovery of related compounds like H1152 in follow-up studies. H-1152 allows for very efficient seeding of individualized HES cells in 96-well plates (similar to HA-100 but at 10-fold lower concentration), enabling HES cell-based small molecule screening. Individualized HES cells that are otherwise passaged in cell clumps allow more uniform cell densities per well, which is a stringent prerequisite for cell-based small molecule screening. The inventors also reasoned that the current small molecule (HA-100) and a related compound H1152 were sufficient for passaging human ES cells.

The inventors used a small molecule library (2000 compounds with known bioactivity) to screen for compounds that may have the ability to increase hematopoiesis. The inventors have demonstrated that the system described above is capable of plating HES cells in 96-well format to provide a platform for small molecule screening as well as screening of other agents and conditions. The inventors have derived a screening assay and protocol suitable for automation that uses directed differentiation methods leading to hematopoietic precursors. The inventors have successfully performed a screen under these conditions and identified 28 initial candidate compounds which are now being validated. Although the performance of the screen can be further improved through a more thorough assay development, the key goal of plating HES cells for automated screening has been accomplished. This platform allows for the production of large quantities of these cells that are otherwise difficult to obtain in quantities required for studies involved in screens, toxicology testing and target validation. The alternative source (cells isolated from blood and bone marrow) offers only limited quantities and can not provide a stable genetic background, due to the fact that batches from different donors have to be pooled. Using these methods, cells with reproducible quality may be provided to the research community.

The assay used in this protocol was developed based on an ELISA protocol which can detect the presence of two characteristic cell surface markers (CD34 and CD43). These markers identify potent hematopoietic precursors that the inventors can subsequently isolate to differentiate the cells into the desired blood lineages or provide as such as a starting material. The inventors used the automated platform to seed individualized human ES cells in 96-well plates and grow them for four days. Then the media was switched to defined differentiation media and compound to be screened was added by the robot to a final concentration of 20 micromolar using a 96-channel pin tool. After four days exposure to the compound including an addition of media after two days the media was changed to a growth factor reduced differentiation media and maintained for 6 more days (with media changes every other day) until the cells are subjected to the ELISA protocol for final readout. The timeline of this experiment was developed for differentiation media only. The inventors have obtained 1-6% CD43 and 2-25% CD34 positive cells by this method. The screen was designed to detect compounds that further increase the population of potent hematopoietic precursors to increase production. Due to issues with the CD34 antibody, data for only CD43 expression was obtained. Nonetheless, the population of CD43 positive cells is likely the most important marker to identify a commitment to the blood lineages.

The inventors were able to use the AmplexUltraRed and the SensiFlex assays (Invitrogen) in a multiplex ELISA and did show with controls, that these assays were compatible and offer the possibility for SCP to simultaneously screen for two cell markers (on the surface or inside the cells, after addition of a separate wash step in the protocol). This is particularly important when screening for cell lineages that require more than one marker for sufficient recognition. A high rate of false positives amongst control DMSO wells at the edge of some plates as well as an accumulation of hits among the top and bottom row of some plates. Although this last study conducted yielded preliminary data, the inventors this screening assay may be optimized at the stage of the ELISA, through better washing procedures and with optimized antibodies and concentrations, as has been demonstrated in other ELISA screens. Nonetheless, successfully providing HES cells for screening in 96-well plates represents a key accomplishment.

In this application the inventors were able to obtain very good homogeneity in plating into 96-well plates using a modified procedure established above. For this purpose however the inventors plated 16,000 cells per well, which is a 5-fold higher seeding density, than in the regular propagation and maintenance of undifferentiated HES cells with the automated procedure. This particular change was used in order to accommodate attachment to an alternate proprietary matrix other than Matrigel, which turned out to be a crucial step in the differentiation protocol. Successful seeding in 96-well format to facilitate robust screening may be used.

Although the inventors had the capacity to perform the media changes for this screen with the automated liquid handling system at hand, the inventors decided in the interest of time and money, to change media and perform the ELISA assay, by aspirating manually using a vacuum 12-channel wand and dispensing using an automated dispenser without stacker. While the inventors did not take advantage of the reproducibility of a fully automated system, the inventors saved significant time and reagents. A Matrix Wellmate automated dispenser was used.

The above examples demonstrate a successfully automated HES cell culture and maintenance. The above data demonstrates that the inventors were able to solve the major challenges towards providing an automatable procedure for HES cell culture. The inventors further anticipate that additional throughput can be achieved via optimization of the system. The inventors anticipate that improved quality control, monitoring of cell growth, and improved passaging can be achieved using the above system. It is anticipated that with an optimized procedure, one may not need to identify and isolate differentiated impurities as is necessary in manual protocols.

The above system may be easily modified to include a liquid handling system like the Tecan Cellerity system, which has been successfully established for maintenance of other attached cell lines. The major step towards the application of such a system was the use of trypsin to passage cells. An independent publication by Watanabe et al. Nat Biotech (2007) "A ROCK inhibitor permits survival of dissociated human embryonic stem cells" supports the ability of HA-100 to maintain HES cell growth.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,284,412
U.S. Pat. No. 4,352,883
U.S. Pat. No. 4,498,766
U.S. Pat. No. 4,661,913
U.S. Pat. No. 4,714,682
U.S. Pat. No. 4,767,206
U.S. Pat. No. 4,774,189
U.S. Pat. No. 4,857,451
U.S. Pat. No. 4,989,977
U.S. Pat. No. 5,160,974
U.S. Pat. No. 5,478,722
U.S. Pat. No. 5,843,780
U.S. Pat. No. 6,200,806
U.S. Pat. No. 6,325,114
U.S. Pat. No. 7,029,913
U.S. Publn. 2006/0084168
U.S. Publn. 2006/0198827
U.S. Publn. 2006/0210596
Davies et al., *Biochem. J.*, 351:95-105, 2000.
Griffiths, In: *Animal Cell Biotechnology*, 3:179-220, Spier and Griffiths (Eds.), Academic Press, London, 1986.
Ikenoya, et al., *J. Neurochem.*, 81:9, 2002.
Ludwig & Thompson, *Human Cell Culture*, 6:1-16, 2007.
Ludwig et al., *Nat. Biotechnol.*, 24:185-187, 2006a.
Ludwig et al., *Nat. Methods*, 3(8):637-646, 2006b.
Maekawa et al., Science, 389:895-898, 1999
PCT Appln. WO 94/17178
Sasaki et al.; *Pharmacol. Ther.*, 93:225, 2002.
Takahashi et al., *Cell*, 126(4):663-676, 2006.
Takahashi et al., *Cell*, 126(4):663-76, 2007.
Terstegge et al., *Biotech. Bioengin.*, 96(1):195-201, 2007.
Thomson et al., *Science*, 282(5391):1145-1147, 1998.
Van Wezel, *Nature*, 216(110):64-65, 1967.
Wang et al., *Am. J. Physiol.*, 263(4 Pt 1):G480-486, 1992.
Wang et al., *FEBS Letters*, 353:138-142, 1994.
Wang et al., In: *Animal Cell Technology: Basic & Applied Aspects*, Kaminogawa et al. (Eds.), 5:463-469, Kluwer Academic Publishers, Netherlands, 1993.
Watanabe et al., *Nat. Biotech.*, 25(6):681-6, 2007.
Yu et al., *Science*, 318:1917-1920, 2007.

What is claimed is:

1. A method for automated expansion of pluripotent stem cells comprising:
   (a) obtaining a first population of human pluripotent cells in a growth media;
   (b) separating the pluripotent cells with an automated separation system;
   (c) delivering the separated cells in fresh growth media into a plurality of culture wells;
   (d) culturing the pluripotent cells in the growth media in the plurality of culture wells; and
   (e) repeating steps b-d one or more times to provide an expanded population of pluripotent cells;
wherein said culturing does not comprise culturing the pluripotent cells in the presence of fibroblast feeder cells or serum and further wherein the automated separation system comprises contacting the first population of pluripotent cells with a proteolytic enzyme, wherein the proteolytic enzyme is trypsin, recombinant trypsin, a trypsin-like protease or TRYPLE.

2. The method of claim 1, wherein the growth media comprises TeSR media.

3. The method of claim 1, wherein the first population of pluripotent cells is comprised on a cell culture plate.

4. The method of claim 3, wherein the cell culture plate comprises a gel matrix.

5. The method of claim 1, wherein the first population of pluripotent cells is about 60%, 70%, 80% or 90% confluent at the time of cell separation.

6. The method of claim 3, wherein delivering the separated cells in fresh growth media comprises seeding the cells in one or more new cell culture plate(s).

7. The method of claim 6, wherein the surface area of the new cell culture plate(s) is between from about 5 to about 35 times greater than the surface area of the plate comprising the first population of pluripotent cells.

8. The method of claim 7, wherein the surface area of the new cell culture plate(s) is between from about 10 to about 35 times greater than the surface area of the plate comprising the first population of pluripotent cells.

9. The method of claim 1, wherein the proteolytic enzyme is a recombinant enzyme.

10. The method of claim 1, wherein the automated separation system comprises:
   (i) removing the media from the first pluripotent cell population;
   (ii) contacting the pluripotent cells with a proteolytic enzyme; and
   (iii) incubating the cells with a proteolytic enzyme to separate cell clusters.

11. The method of claim 10, wherein a defined media comprising a proteolytic enzyme inhibitor and a Rho-associated kinase (ROCK) inhibitor is added to the solution after step (iii).

12. The method of claim 10, wherein the pluripotent cells are incubated with the proteolytic enzyme for from about 2 to about 10 minutes.

13. The method of claim 10, wherein the pluripotent cells are incubated with the proteolytic enzyme at between about 25° C. and about 40° C.

14. The method of claim 13, wherein the pluripotent cells are incubated with the proteolytic enzyme at about 37° C.

15. The method of claim 10, wherein the automated separation system further comprises:
   (iv) subjecting the incubated cells to mechanical agitation to further separate cell clusters.

16. The method of claim 15, wherein the mechanical agitation comprises subjecting the pluripotent cells to shear forces or aspiration.

17. A method for automated expansion of pluripotent stem cells comprising:
   (a) obtaining a first population of human pluripotent cells in a growth media;
   (b) separating the pluripotent cells with an automated separation system;
   (c) delivering the separated cells in fresh growth media into a plurality of culture wells;
   (d) culturing the pluripotent cells in the growth media in the plurality of culture wells; and
   (e) repeating steps b-d one or more times to provide an expanded population of pluripotent cells;
wherein said culturing does not comprise culturing the pluripotent cells in the presence of fibroblast feeder cells or serum and further wherein the fresh growth media comprises an inhibitor of a proteolytic enzyme, wherein the fresh growth media comprises an inhibitor of the proteolytic enzyme used for cell separation, wherein the proteolytic enzyme inhibitor is a trypsin inhibitor.

18. The method of claim 17, wherein the proteolytic enzyme inhibitor is a soybean trypsin inhibitor.

19. The method of claim 18, wherein the fresh growth media comprises about 0.5 mg/ml of soybean trypsin inhibitor.

20. A method for automated expansion of pluripotent stem cells comprising:
(a) obtaining a first population of human pluripotent cells in a growth media;
(b) separating the pluripotent cells with an automated separation system;
(c) delivering the separated cells in fresh growth media into a plurality of culture wells;
(d) culturing the pluripotent cells in the growth media in the plurality of culture wells; and
(e) repeating steps b-d one or more times to provide an expanded population of pluripotent cells;
wherein said culturing does not comprise culturing the pluripotent cells in the presence of fibroblast feeder cells or serum, wherein the growth media comprises a effective amount of a Rho-associated kinase (ROCK) inhibitor, wherein the Rho-associated kinase (ROCK) inhibitor is HA-100 or H-1135.

21. The method of claim 20, wherein the Rho-associated kinase (ROCK) inhibitor is HA-100.

22. The method of claim 21, wherein the HA-100 is present in a concentration of about 10 μM.

23. The method of claim 20, wherein the Rho-associated kinase (ROCK) inhibitor is H-1135.

24. The method of claim 23, wherein the H-1135 is present in a concentration of about 1-3 μM.

25. A method for automated expansion of pluripotent stem cells comprising:
(a) obtaining a first population of human pluripotent cells in a growth media;
(b) separating the pluripotent cells with an automated separation system;
(c) delivering the separated cells in fresh growth media into a plurality of culture wells;
(d) culturing the pluripotent cells in the growth media in the plurality of culture wells; and
(e) repeating steps b-d one or more times to provide an expanded population of pluripotent cells;
wherein said culturing does not comprise culturing the pluripotent cells in the presence of fibroblast feeder cells or serum and further wherein no or essentially no differentiation occurs in at least 97% of the expanded population of pluripotent cells, and wherein the pluripotent cells are ES cells.

26. The method of claim 25, wherein the growth media comprises TeSR media.

27. The method of claim 25, wherein the first population of pluripotent cells is comprised on a cell culture plate.

28. The method of claim 27, wherein the cell culture plate comprises a gel matrix.

29. A method for automated expansion of pluripotent stem cells comprising:
(a) obtaining a first population of human pluripotent cells in a growth media;
(b) separating the pluripotent cells with an automated separation system;
(c) delivering the separated cells in fresh growth media into a plurality of culture wells;
(d) culturing the pluripotent cells in the growth media in the plurality of culture wells; and
(e) repeating steps b-d one or more times to provide an expanded population of pluripotent cells;
wherein said culturing does not comprise culturing the pluripotent cells in the presence of fibroblast feeder cells or serum wherein the first population of pluripotent cells is comprised on a cell culture plate and further wherein the first population of pluripotent cells is between about 50% and about 99% confluent at the time of cell separation, and wherein the pluripotent cells are ES cells.

30. The method of claim 29, wherein the first population of pluripotent cells is about 60%, 70%, 80% or 90% confluent at the time of cell separation.

31. The method of claim 29, wherein delivering the separated cells in fresh growth media comprises seeding the cells in one or more new cell culture plate(s).

32. The method of claim 31, wherein the surface area of the new cell culture plate(s) is between from about 5 to about 35 times greater than the surface area of the plate comprising the first population of pluripotent cells.

33. The method of claim 32, wherein the surface area of the new cell culture plate(s) is between from about 10 to about 35 times greater than the surface area of the plate comprising the first population of pluripotent cells.

34. A method for automated expansion of pluripotent stem cells comprising:
(a) obtaining a first population of human pluripotent cells in a growth media;
(b) separating the pluripotent cells with an automated separation system;
(c) delivering the separated cells in fresh growth media into a plurality of culture wells;
(d) culturing the pluripotent cells in the growth media in the plurality of culture wells; and
(e) repeating steps b-d one or more times to provide an expanded population of pluripotent cells;
wherein said culturing does not comprise culturing the pluripotent cells in the presence of fibroblast feeder cells or serum and further wherein the automated separation system comprises contacting the first population of pluripotent cells with a proteolytic enzyme, and wherein the pluripotent cells are ES cells.

35. The method of claim 34, wherein the proteolytic enzyme is trypsin.

36. The method of claim 34, wherein the proteolytic enzyme is recombinant trypsin, a trypsin-like proteinase, or TRYPLE.

37. The method of claim 34, wherein the proteolytic enzyme is a recombinant enzyme.

38. The method of claim 34, wherein the fresh growth media comprises an inhibitor of the proteolytic enzyme used for cell separation.

39. The method of claim 34, wherein the automated separation system comprises:
(i) removing the media from the first pluripotent cell population;
(ii) contacting the pluripotent cells with a proteolytic enzyme; and
(iii) incubating the cells with a proteolytic enzyme to separate cell clusters.

40. The method of claim 39, wherein a defined media comprising a proteolytic enzyme inhibitor and a Rho-associated kinase (ROCK) inhibitor is added to the solution after step (iii).

41. The method of claim 34, wherein the pluripotent cells are incubated with the proteolytic enzyme for from about 2 to about 10 minutes.

42. The method of claim 34, wherein the pluripotent cells are incubated with the proteolytic enzyme at between about 25° C. and about 40° C.

43. The method of claim 42, wherein the pluripotent cells are incubated with the proteolytic enzyme at about 37° C.

44. The method of claim 34, wherein the automated separation system further comprises:
   (iv) subjecting the incubated cells to mechanical agitation to further separate cell clusters.

45. The method of claim 44, wherein the mechanical agitation comprises subjecting the pluripotent cells to shear forces or aspiration.

46. A method for automated expansion of pluripotent stem cells comprising:
   (a) obtaining a first population of human pluripotent cells in a growth media;
   (b) separating the pluripotent cells with an automated separation system;
   (c) delivering the separated cells in fresh growth media into a plurality of culture wells;
   (d) culturing the pluripotent cells in the growth media in the plurality of culture wells; and
   (e) repeating steps b-d one or more times to provide an expanded population of pluripotent cells;
wherein said culturing does not comprise culturing the pluripotent cells in the presence of fibroblast feeder cells or serum and further wherein the fresh growth media comprises an inhibitor of a proteolytic enzyme, and wherein the pluripotent cells are ES cells.

47. The method of claim 46, wherein the proteolytic enzyme inhibitor is a trypsin inhibitor.

48. The method of claim 47, wherein the proteolytic enzyme inhibitor is a soybean trypsin inhibitor.

49. The method of claim 48, wherein the fresh growth media comprises about 0.5 mg/ml of soybean trypsin inhibitor.

50. The method of claim 46, further comprising replacing the growth media comprising the proteolytic enzyme inhibitor with a growth media that is essentially free of said inhibitor.

51. A method for automated expansion of pluripotent stem cells comprising:
   (a) obtaining a first population of human pluripotent cells in a growth media;
   (b) separating the pluripotent cells with an automated separation system;
   (c) delivering the separated cells in fresh growth media into a plurality of culture wells;
   (d) culturing the pluripotent cells in the growth media in the plurality of culture wells; and
   (e) repeating steps b-d one or more times to provide an expanded population of pluripotent cells;
wherein said culturing does not comprise culturing the pluripotent cells in the presence of fibroblast feeder cells or serum and further wherein the separation system is automated by a liquid handler robot, and wherein the pluripotent cells are ES cells.

52. The method of claim 51, wherein the population of pluripotent cells is free or essentially free from non-pluripotent cells.

53. A method for automated expansion of pluripotent stem cells comprising:
   (a) obtaining a first population of human pluripotent cells in a growth media;
   (b) separating the pluripotent cells with an automated separation system;
   (c) delivering the separated cells in fresh growth media into a plurality of culture wells;
   (d) culturing the pluripotent cells in the growth media in the plurality of culture wells; and
   (e) repeating steps b-d one or more times to provide an expanded population of pluripotent cells;
wherein said culturing does not comprise culturing the pluripotent cells in the presence of fibroblast feeder cells or serum, wherein the population of pluripotent cells is free or essentially free from non-pluripotent cells and further wherein the population of pluripotent cells is human induced pluripotent stem cells.

54. A method for automated expansion of pluripotent stem cells comprising:
   (a) obtaining a first population of human pluripotent cells in a growth media;
   (b) separating the pluripotent cells with an automated separation system;
   (c) delivering the separated cells in fresh growth media into a plurality of culture wells;
   (d) culturing the pluripotent cells in the growth media in the plurality of culture wells; and
   (e) repeating steps b-d one or more times to provide an expanded population of pluripotent cells;
wherein said culturing does not comprise culturing the pluripotent cells in the presence of fibroblast feeder cells or serum, wherein the growth media comprises a effective amount of a Rho-associated kinase (ROCK) inhibitor, and wherein the pluripotent cells are ES cells.

55. The method of claim 54, wherein the Rho-associated kinase (ROCK) inhibitor is HA-100.

56. The method of claim 55, wherein the HA-100 is present in a concentration of about 10 µM.

57. The method of claim 54, wherein the Rho-associated kinase (ROCK) inhibitor is H-1135.

58. The method of claim 57, wherein the H-1135 is present in a concentration of about 1-3 µM.

\* \* \* \* \*

UNITED STATES PATENT AND TRADEMARK OFFICE
CERTIFICATE OF CORRECTION

| | |
|---|---|
| PATENT NO. | : 8,815,585 B2 |
| APPLICATION NO. | : 12/164969 |
| DATED | : August 26, 2014 |
| INVENTOR(S) | : Nathaniel Beardsley et al. |

It is certified that error appears in the above-identified patent and that said Letters Patent is hereby corrected as shown below:

In title page, col. 2, item (56) References Cited - Other Publications, delete the 10th reference on page 1 "International Search Report and Written Opinion, issued in Application No. PCT/US2008, dated Aug. 20, 2008." and replace with --International Search Report and Written Opinion, issued in Application No. PCT/US2008/068814, dated Aug. 20, 2008.-- therefor.

Signed and Sealed this
Thirtieth Day of December, 2014

Michelle K. Lee
*Deputy Director of the United States Patent and Trademark Office*